(12) United States Patent
Grace et al.

(10) Patent No.: US 6,334,099 B1
(45) Date of Patent: Dec. 25, 2001

(54) METHODS FOR NORMALIZATION OF EXPERIMENTAL DATA

(75) Inventors: Dennis R. Grace, San Diego; Jayson T. Durham, Lakeside, both of CA (US)

(73) Assignee: Digital Gene Technologies, Inc., La Jolla, CA (US)

( * ) Notice: Subject to any disclaimer, the term of this patent is extended or adjusted under 35 U.S.C. 154(b) by 0 days.

(21) Appl. No.: 09/318,679

(22) Filed: May 25, 1999

(51) Int. Cl.[7] .................................................. G06F 17/00
(52) U.S. Cl. ........................ 702/194; 702/19; 702/20; 702/21; 702/22; 435/6
(58) Field of Search .................................. 702/19, 20, 21, 702/22, 23, 25, 26, 27–32, 66, 70, 71, 73, 74, 75–78, 127–129, 179, 182, 183, 189, 190, 193, 196, 197, FOR 103, 106, 115–119, 134, 135, 139, 140, 141, 164, 168, 171; 708/300–303; 435/5, 6, 91.1, 91.2; 707/1, 104; 345/302

(56) References Cited

U.S. PATENT DOCUMENTS 3,742,202 6/1973 Spreitzhofer .
4,811,218 3/1989 Hunkapiller et al. .

(List continued on next page.)

FOREIGN PATENT DOCUMENTS

WO 98/00708 1/1998 (WO) .
WO 99/05323 2/1999 (WO) .

(List continued on next page.)

OTHER PUBLICATIONS

Giddings, et al., "An adaptive object–oriented strategy for base calling in DNA sequence analysis," *Nucleic Acids Research*, 1993, vol. 21, No. 19, pp. 4530–4540.

(List continued on next page.)

*Primary Examiner*—Marc S. Hoff
*Assistant Examiner*—Carol S Tsai
(74) *Attorney, Agent, or Firm*—McDonnell Boehnen Hulbert & Berghoff; Stephen Lesavich

(57) ABSTRACT

Methods for normalization of experimental data with experiment-to-experiment variability. The experimental data may include biotechnology data or other data where experiment-to-experiment variability is introduced by an environment used to conduct multiple iterations of the same experiment. Deviations in the experimental data are measured between a central character and data values from multiple indexed data sets. The central character is a value of an ordered comparison determined from the multiple indexed data sets. The central character includes zero-order and low order central characters. Deviations between the central character and the multiple indexed data sets are removed by comparing the central character to the measured deviations from the multiple indexed data sets, thereby reducing deviations between the multiple indexed data sets and thus reducing experiment-to-experiment variability. Preferred embodiments of the present invention may be used to reduce intra-experiment and inter-experiment variability. When experiment-to-experiment variability is reduced or eliminated, comparison of experimental results can be used with a higher degree of confidence. Experiment-to-experiment variability is reduced for biotechnology data with new methods that can be used for bioinformatics or for other types of experimental data that are visual displayed (e.g., telecommunications data, electrical data for electrical devices, optical data, physical data, or other data). Experimental data can be consistently collected, processed and visually displayed with results that are accurate and not subject to experiment-to-experiment variability. Thus, intended experimental goals or results (e.g., determining polynucleotide sequences such as DNA, cDNA, or mRNA sequences) may be achieved in a more efficient and effective manner.

11 Claims, 21 Drawing Sheets

U.S. PATENT DOCUMENTS

| | | | |
|---|---|---|---|
| 4,847,559 | | 7/1989 | Keren . |
| 5,002,867 | * | 3/1991 | Macevicz ................................. 435/6 |
| 5,119,316 | * | 6/1992 | Dam et al. ........................... 364/498 |
| 5,365,455 | * | 11/1994 | Tibbetts et al. ...................... 364/497 |
| 5,419,825 | | 5/1995 | Fujii . |
| 5,459,037 | | 10/1995 | Sutcliffe et al. . |
| 5,606,512 | * | 2/1997 | Strickland ........................... 364/499 |
| 5,683,881 | * | 11/1997 | Skiena ..................................... 435/6 |
| 5,712,476 | | 1/1998 | Renfrew et al. . |
| 5,766,875 | * | 6/1998 | Hafeman et al. ....................... 435/29 |
| 5,777,888 | | 7/1998 | Rine et al. . |
| 5,786,142 | | 7/1998 | Renfrew et al. . |
| 5,807,680 | | 9/1998 | Sutcliffe et al. . |
| 5,853,979 | * | 12/1998 | Green et al. ............................. 435/5 |
| 5,916,747 | * | 6/1999 | Gilchrist et al. ......................... 435/6 |
| 6,027,941 | * | 2/2000 | Jarvie et al. ......................... 436/173 |
| 6,138,077 | * | 10/2000 | Brenner ................................. 702/19 |
| 6,199,017 | * | 3/2001 | Tomonaga et al. .................... 702/19 |
| 6,236,944 | * | 5/2001 | Miller et al. ........................... 702/19 |
| 6,253,162 | * | 6/2001 | Jarman et al. ....................... 702/179 |
| 6,269,312 | * | 7/2001 | Mayo et al. ........................... 702/19 |

FOREIGN PATENT DOCUMENTS

| | | |
|---|---|---|
| WO 99/05324 | 2/1999 | (WO) . |
| WO 00/22173 | 4/2000 | (WO) . |

OTHER PUBLICATIONS

Verbeek, et al., "2–D adaptive smoothing by 3–D distance transformation," *Pattern Recognition Letters*, Jan. 1989, vol. 9, No. 1, pp. 53–65.

Lucke, et al., "A Digit–Serial Architecture for Gray–Scale Morphological Filtering, " *IEEE Transactions on Image Processing*, Mar. 1995, vol. 4, No. 3, pp. 387–391.

Artunian, et al., "Flexible Software Architecture for User–Interface and Machine Control in Laboratory Automation," *Bio Techniques* Oct. 1998, vol. 25, No. 4, pp. 698–705.

* cited by examiner

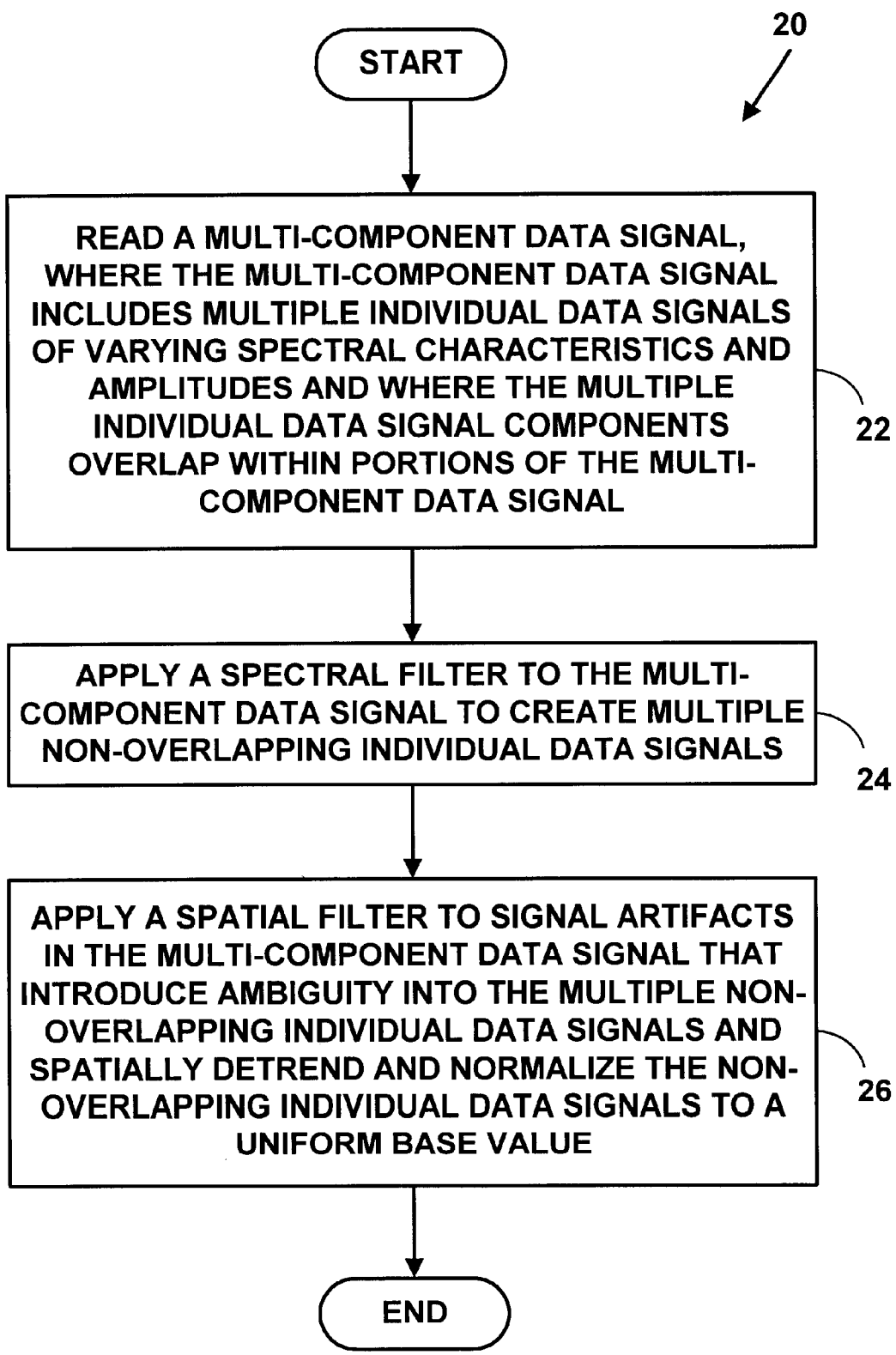

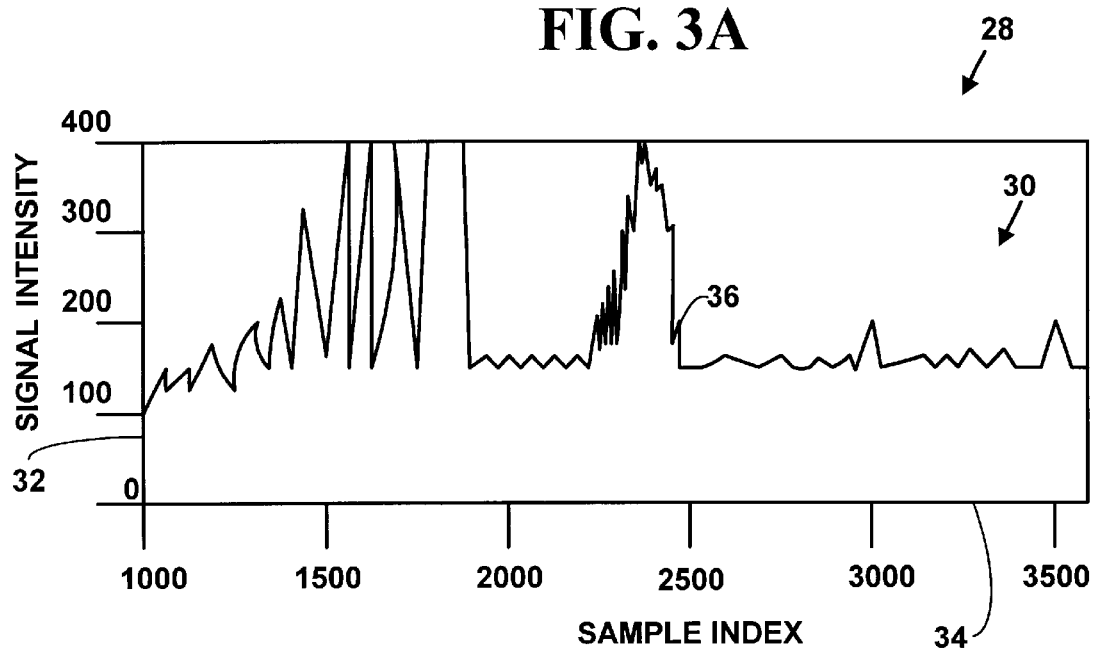
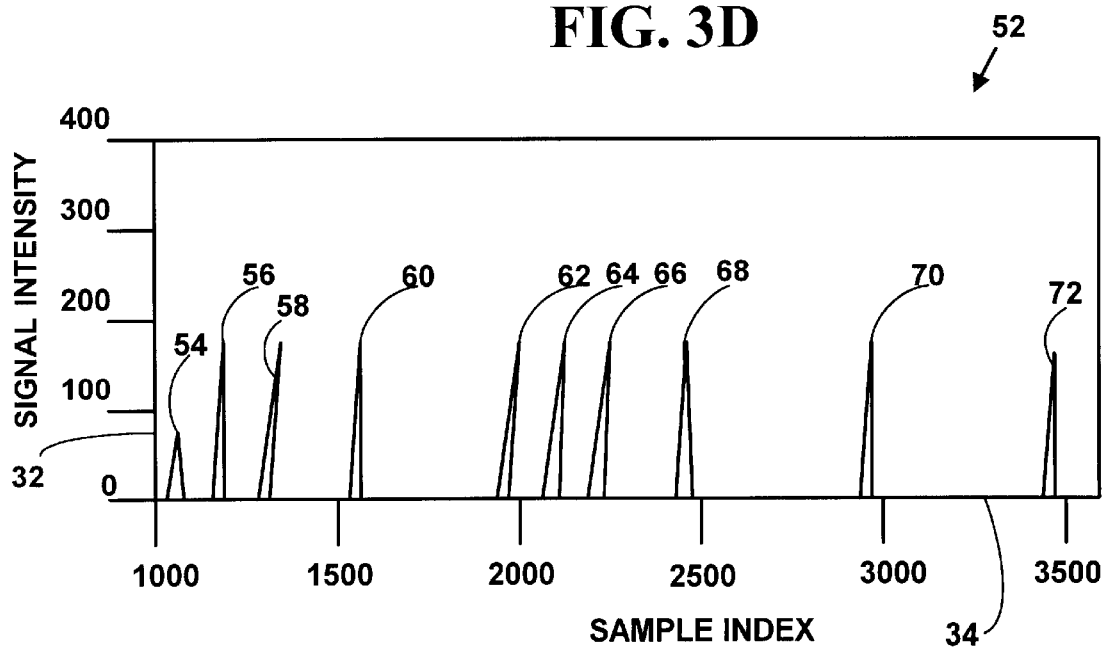

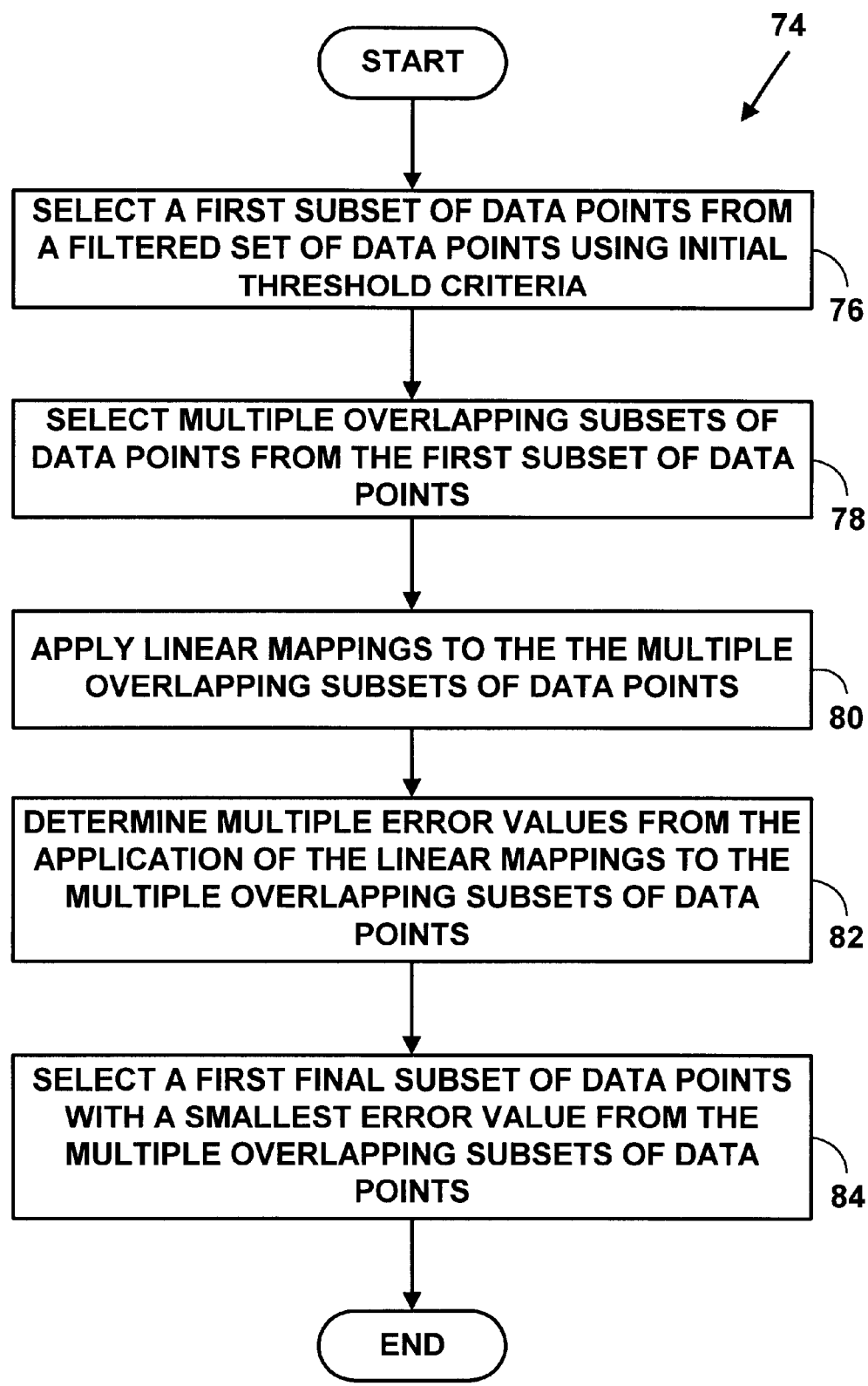

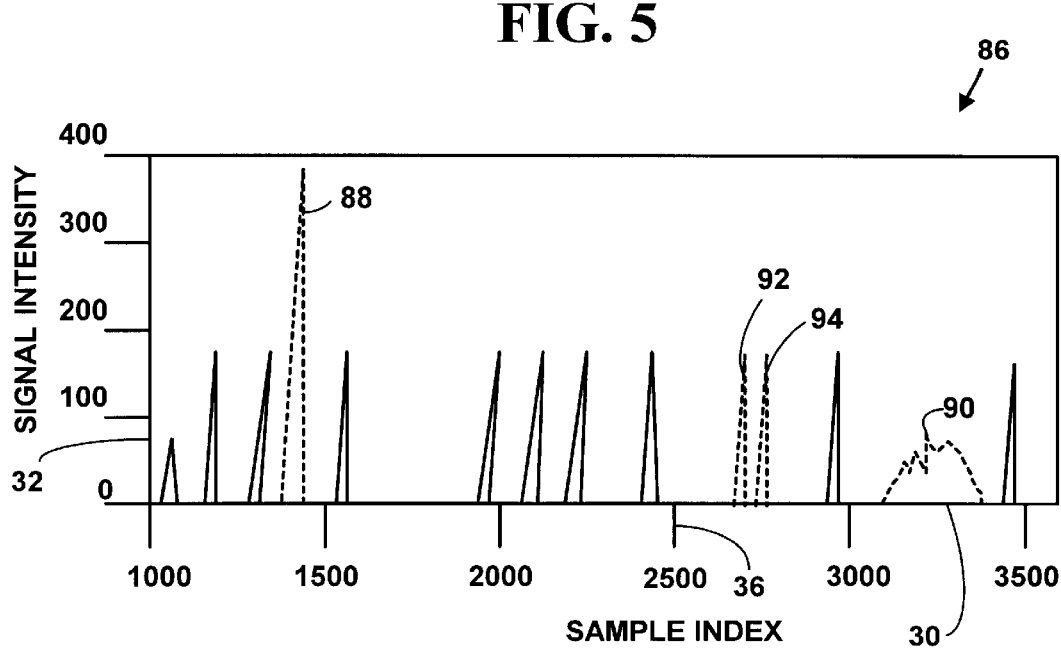
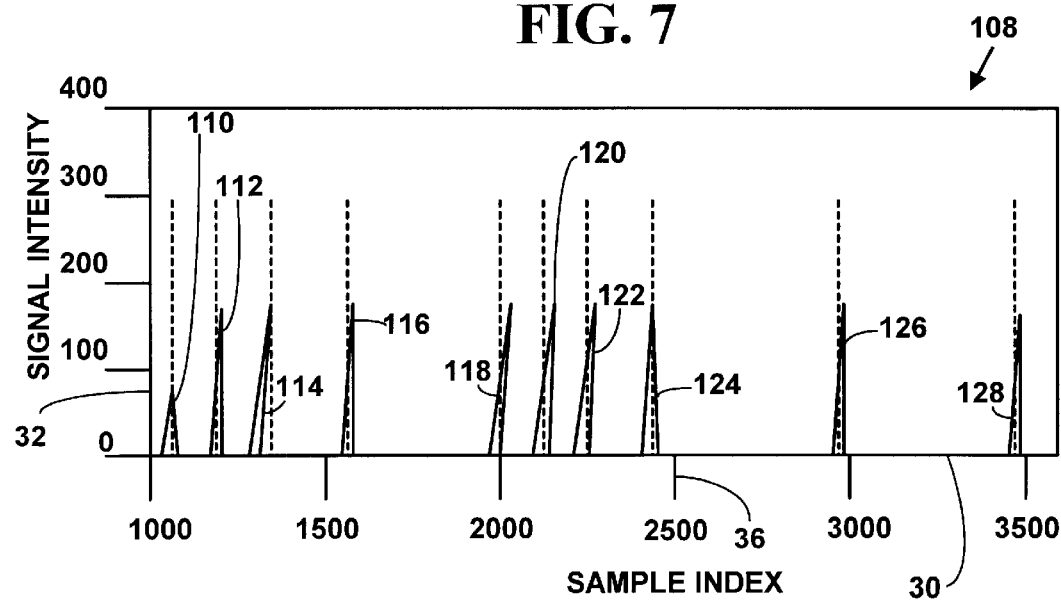

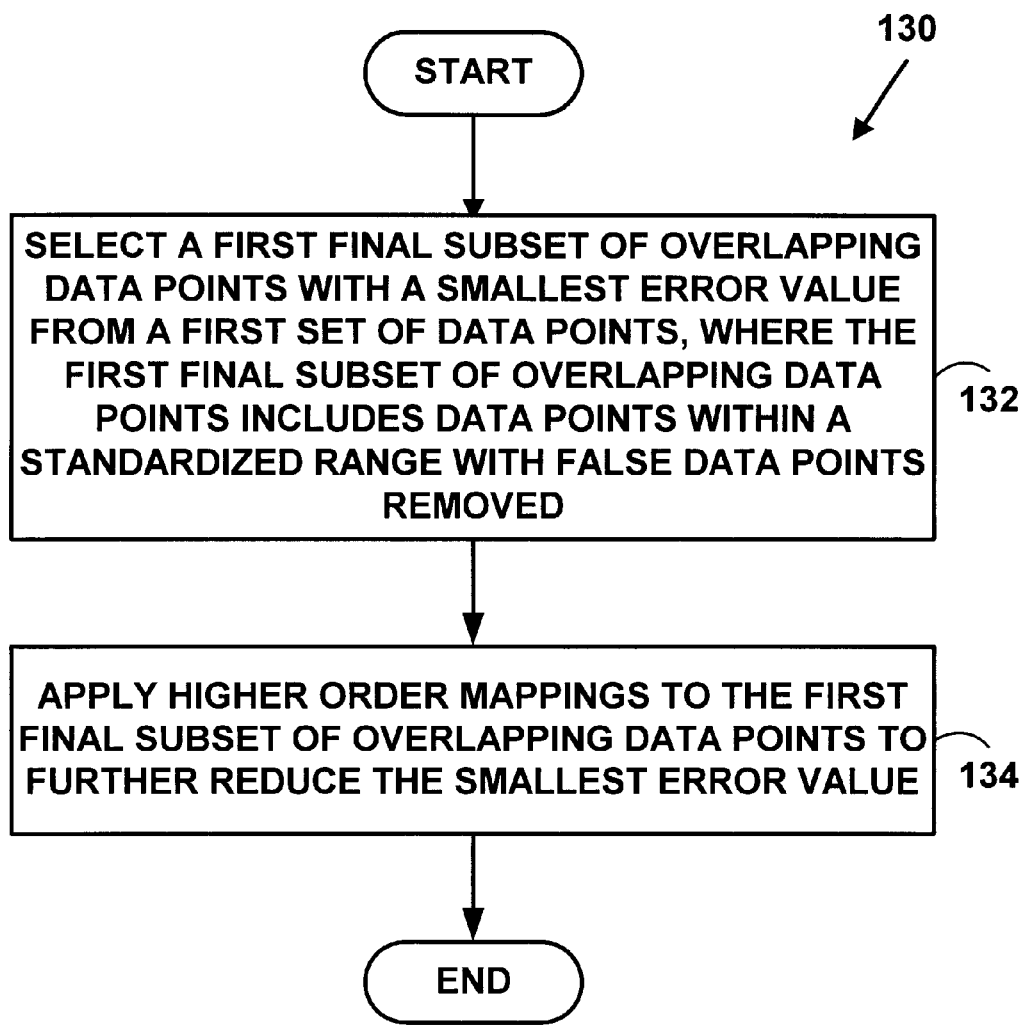

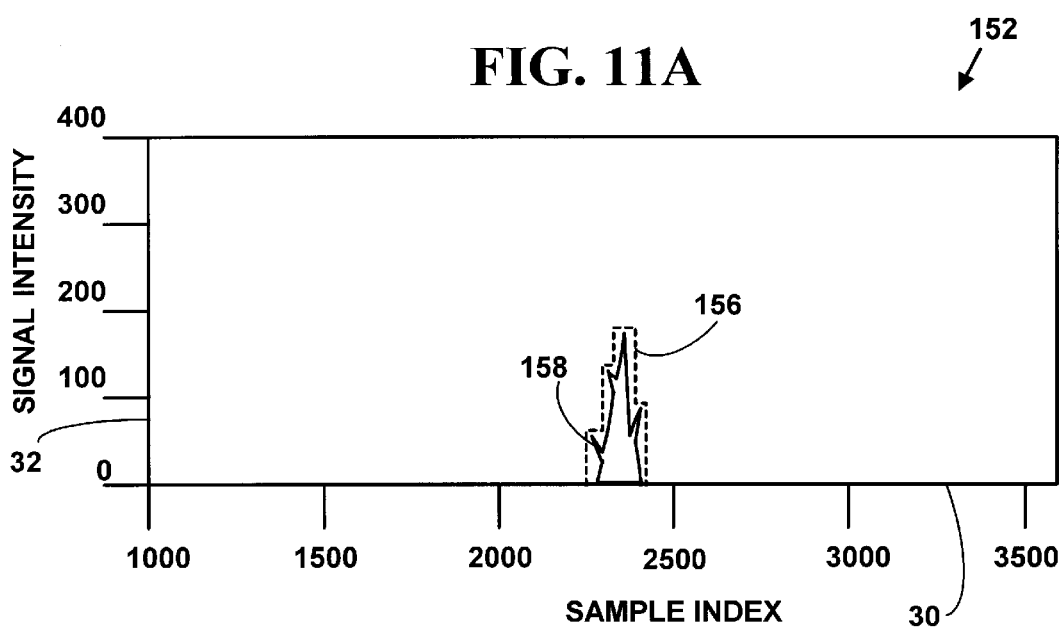
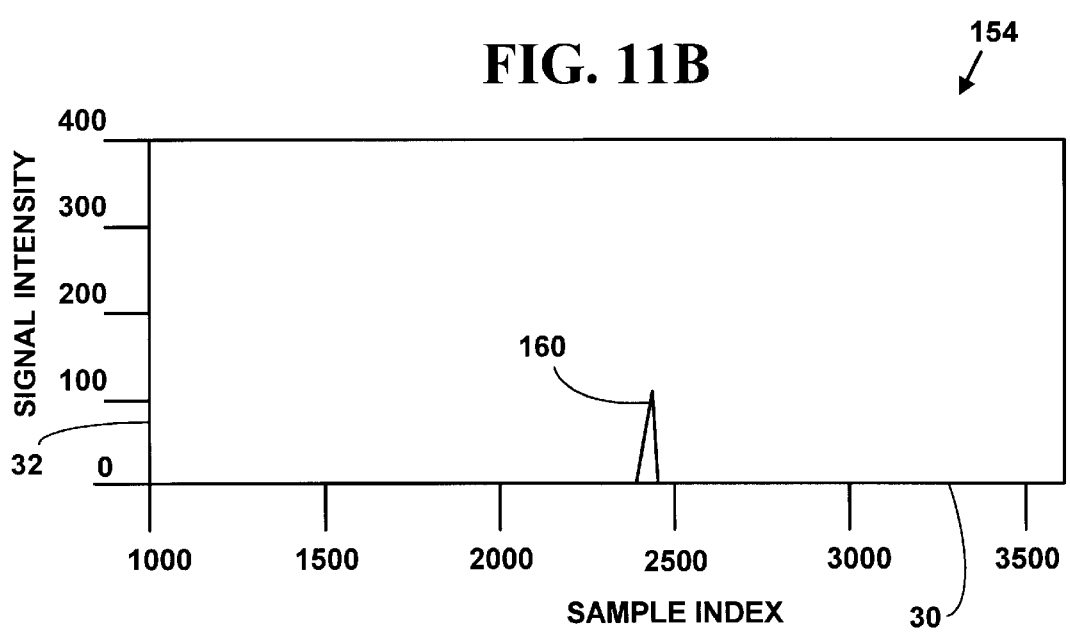

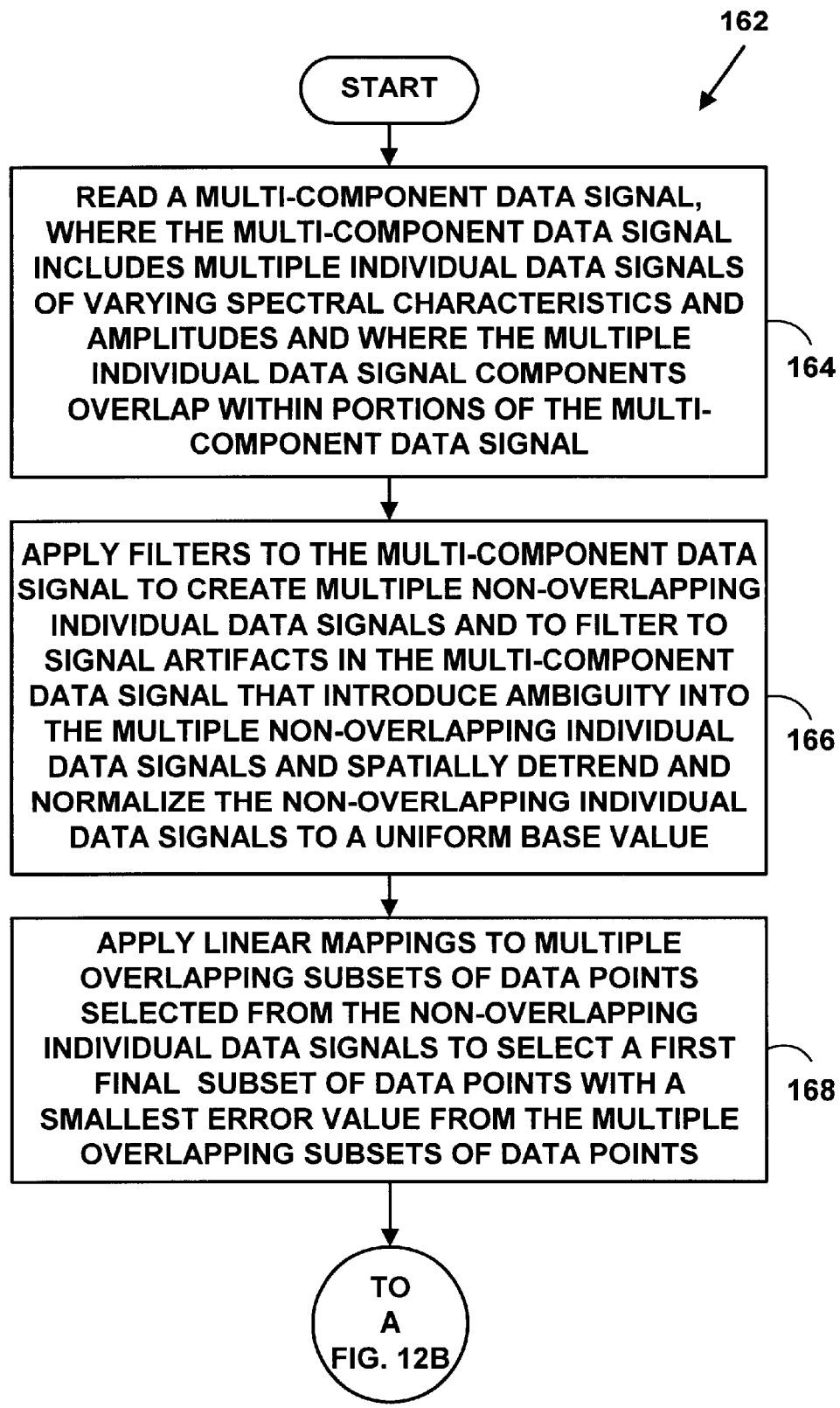

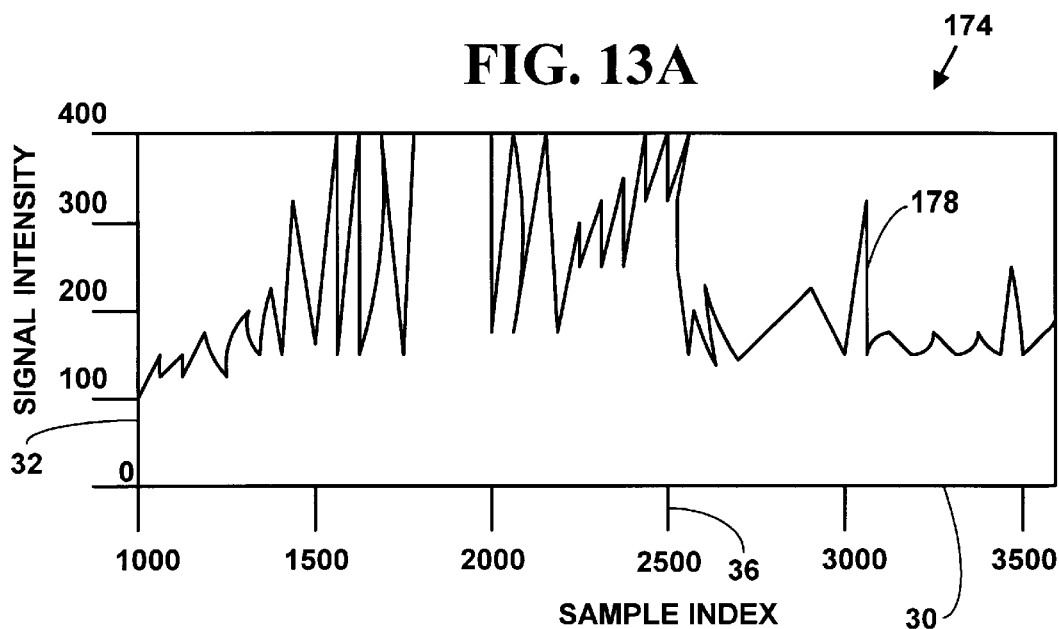
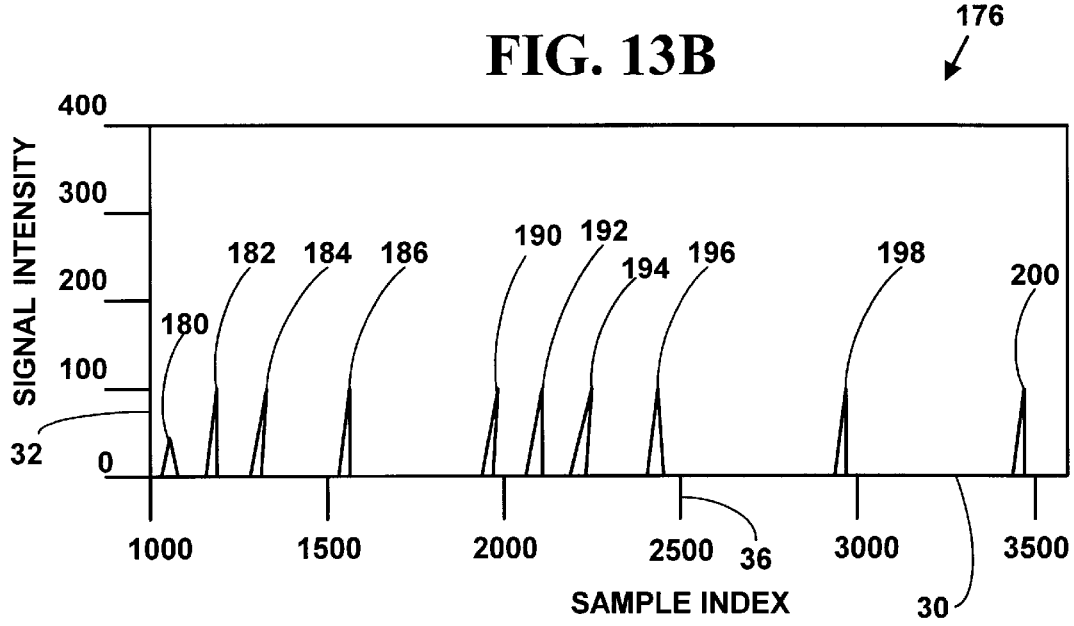

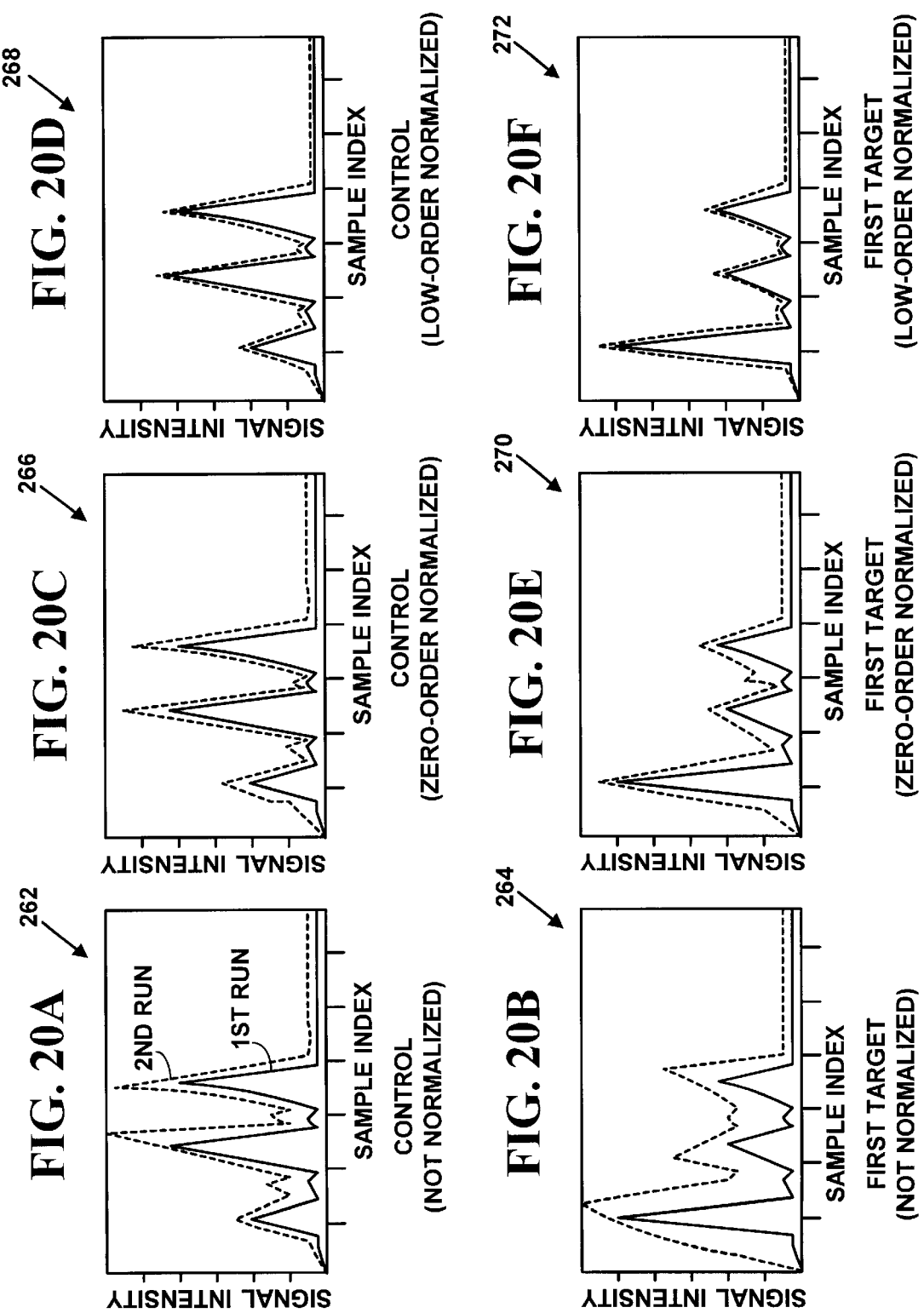

METHODS FOR NORMALIZATION OF EXPERIMENTAL DATA

FIELD OF THE INVENTION

This invention relates to normalizing experimental data. More specifically, it relates to methods for normalizing experimental data, such as biotechnology data, to reduce experiment-to-experiment variability.

BACKGROUND OF THE INVENTION

Biotechnology data is collected and analyzed for many diverse purposes. As is known in the art, biotechnology data typically includes data obtained from biological systems, biological processes, biochemical processes, biophysical processes, or chemical processes. For example, sequences of deoxyribonucleic acid ("DNA") from many different types of living organisms are often determined and mapped. DNA is double-stranded polynucleotide including a continuous string of four nucleotide base elements. The four nucleotide base elements include deoxyadenosine, deoxycytidine, deoxyguanosine, and deoxythymidine. The four nucleotide bases are usually abbreviated as "A," "C," "G" and "T" respectively. DNA is used to make ribonucleic acid ("RNA"), which in turn is used to make proteins. "Genes" include regions of DNA that are transcribed into RNA, which encodes a translated protein.

One fundamental goal of biochemical research is to map and characterize all of the protein molecules from genes in a living organism. The existence and concentration of protein molecules typically help determine if a gene is "expressed" or "repressed" in a given situation. Protein characterization includes, identification, sequence determination, expression, characteristics, concentrations and biochemical activity. Responses of proteins to natural and artificial compounds are used to develop new treatments for diseases, improve existing drugs, develop new drugs and for other medical and scientific applications.

Biotechnology data is inherently complex. For example, DNA sequences include large numbers of A's, C's, G's and T's, that need to be stored and retrieved in a manner that is appropriate for analysis. There are a number of problems associated with collecting, processing, storing and retrieving biotechnology data using "bioinformatics" techniques known in the art. As is known in the art, bioinformatics is the systematic development and application of information technologies and data mining techniques for processing, analyzing and displaying data obtained by experiments, modeling, database searching and instrumentation to make observations about biological processes. Biotechnology data is commonly presented as graphical plots of two or more variables. A "peak," i.e., a local maximum in a plot of two or more variables, is often a feature of interest in biotechnology data.

When biotechnology data is collected, the collection process often introduces variability based on an environment used to conduct the experiment. For example, DNA sequences may be determined by processing samples using gel-electrophoresis. A label (e.g., a dye) is incorporated into the samples placed on gel-plates for detection by laser-induced fluorescence.

Gel-electrophoresis resolves molecules from the samples into distinct bands of measurable lengths on a gel plate. Gel-plates created with different batches of the same gel may be used to complete the same experiment, with the same target (e.g., the same polynucleotide sample), multiple times. All of the experiments should ideally yield the same results, since the same target is used in the same experiment. However, the gel-electrophoresis process typically introduces small errors in the biotechnology data due to variability in the gel-electrophoresis process.

For example, a gel may have been prepared by two different lab technicians, may have come from two packages of the same product, may have been purchased at different times, or may be applied to gel-plates at slightly different consistency or thickness, either by a lab technician or by with an automated process (e.g., a robot), etc. These factors and other factors typically introduce "experiment-to-experiment variability" into an experiment completed multiple times that ideally should yield exactly the same results.

Another problem is that biotechnology data is also collected with micro-arrays. Micro-arrays can also be used to provide sequence information instead of gel-electrophoresis. Micro-arrays may also introduce variability into the same experiment due to variations in sample preparation for the micro-arrays. Yet another problem is that biotechnology data that is data collected with experiment-to-experiment variability typically only grossly appropriate for visual display using bioinformatics techniques known in the art.

As is known in the art, one of the most commonly used methodologies in biotechnology is "comparison." Many biological objects are associated with families that share the same structural or functional features. For example, many proteins with a similar sequence may have common functionality. If a protein with a sequence similar to a known protein is located, the located protein may have a common functionality, and thus may have a common response to an environmental condition (e.g., a new drug).

Visual display of biotechnology data is typically recognized as typically being "necessary" for biotechnology research. Visual display tools allow creation of complex views of large amounts of inter-related data. Experimental data is typically displayed using a Graphical User Interface ("GUI") that may include a multiple windowed-display on a computer display.

Visual display and comparative analysis is typically hampered by variability introduced into experimental data. For example, if five iterations of the same experiment with the same target are visually displayed, the output values should ideally be superimposed on one another. However, due to experiment-to-experiment variability, the output values for the five iterations of the experiment typically will differ slightly and a visual display will tend to "magnify" experiment-to-experiment variability. This may lead to confusion during analysis and cause a user to lose confidence in a process used to collect and display experimental data.

In addition, in many instances, experiment-to-experiment variability is of a same order of magnitude as desired experimental results. Using visual display of experimental results with experiment-to-experiment variability, a user may not be able to determine if differences in results are due to a new target (e.g., a new polynucleotide sequence) or experiment-to-experiment variability.

Thus, it is desirable to reduce experiment-to-experiment variability in data obtained from experiments. The reduction of experiment-to-experiment variability should allow visual display and comparative analysis to be completed without confusion or loss of confidence in processes used to collect, process and display experimental data.

SUMMARY OF THE INVENTION

In accordance with preferred embodiments of the present invention, some of the problems associated with experiment-to-experiment variability in experimental data are overcome. Methods for normalization of experimental data are provided. One aspect of the invention includes a method for data normalization of multiple data sets of experimental data. Multiple sets of experimental data are indexed with one or more indices to create multiple indexed data sets. However, other data organization schemes could also be used and the present invention is not limited to indexing multiple data sets. Deviations are measured between a determined central character and data values from the multiple indexed data sets. In one exemplary preferred embodiment of the present invention, the determined central character is a value for an ordered comparison determined from the multiple indexed data sets. Deviations between the determined central character and the multiple indexed data sets are removed by comparing the determined central character to the measured deviations from the multiple indexed data sets, thereby reducing deviations between the multiple indexed data sets and thus reducing experiment-to-experiment variability.

Another aspect of the invention includes applying a central character normalization transform to data values from the multiple indexed data sets to utilize data information across indices from multiple indexed data sets. The normalization transform is applied before the determined central character is used to remove deviations from the multiple indexed data sets. The normalization transform includes, but is not limited to, for example, zero-order normalization transformations and low-order normalization transformations. Yet another aspect of the present invention includes a method for creating a zero-order central character from multiple indexed data sets. The zero-order central character is typically a data-value-independent constant. Yet another aspect of the present invention includes creating a low-order central character from multiple indexed data sets. The low-order central character is typically a data-value-dependent smoothly ranging scaling function.

Preferred embodiments of the present invention may be used to reduce experiment-to-experiment variability. Experimental data may then be consistently collected, processed and visually displayed with a higher degree of confidence that obtained results are accurate and include reduced experiment-to-experiment variability. Thus, intended experimental goals or results (e.g., determining a new polynucleotide sequence) may be achieved in a quicker, and a cost effective manner with reduced experiment-to-experiment variability.

In one exemplary preferred embodiment of the present invention, new methods that can be used for bioinformatics, are used to reduce experiment-to-experiment variability of biotechnology data. However, preferred embodiments of the present invention are not limited to reducing experiment-to-experiment variability for biotechnology data. The present invention may also be used to reduce experiment-to-experiment variably in other types of experimental data, including but not limited to, telecommunications data, electrical data, optical data, physical data, or other experimental data with experiment-to-experiment variability due to an environment used to conduct experiments.

The foregoing and other features and advantages of preferred embodiments of the present invention will be more readily apparent from a detailed description that follows. The detailed description proceeds with references to the accompanying drawings.

BRIEF DESCRIPTION OF THE DRAWINGS

Preferred embodiments of the present invention are described with reference to the following drawings, wherein:

Preferred embodiments of the present invention are described with reference to the following drawings, wherein:

FIG. 2 is a flow diagram illustrating a method for data normalization for a multi-component data signal;

FIG. 3A is a block diagram illustrating an exemplary unfiltered signal intensity trace for a multi-component data signal;

FIG. 3D is a block diagram illustrating a filtered and normalized multi-component data signal using the method from FIG. 2;

FIG. 4 is a flow diagram illustrating a method of clutter rejection;

FIG. 5 is a block diagram illustrating a filtered and normalized multi-component data signal using the method from FIG. 2;

FIG. 7 is a block diagram illustrating data peaks with size standard detection with clutter rejection using the method of FIG. 4;

FIG. 8 is a block diagram illustrating a method for data size calibration;

FIGS. 11A and 11B are block diagrams illustrating envelope detection using the method of FIG. 10;

FIGS. 12A and 12B is a flow diagram illustrating a method for processing multi-component experimental data;

FIGS. 13A and 13B are block diagrams illustrating the method of FIGS. 12A and 12B;

FIG. 20A is a block diagram illustrating a portion of an exemplary output display for an indexed set of a control data for an exemplary experiment;

FIG. 20B is a block diagram illustrating a portion of an exemplary output display for an exemplary indexed set of target data for an exemplary experiment;

FIG. 20C is a block diagram illustrating portion of an exemplary output display for the indexed data set of control data from FIG. 20A normalized with a zero-order normalization;

FIG. 20D is a block diagram illustrating a portion of an exemplary output display for the indexed set of control data from FIG. 20A normalized with a low-order normalization;

FIG. 20E is a block diagram illustrating a portion of an exemplary output display for the indexed data set of target data from FIG. 20B normalized with a low-order normalization; and FIG. 20F is a block diagram illustrating a portion an exemplary output display for the indexed data set of target data from FIG. 20B normalized with a low-order normalization.

DETAILED DESCRIPTION OF PREFERRED EMBODIMENTS

Figure 1:
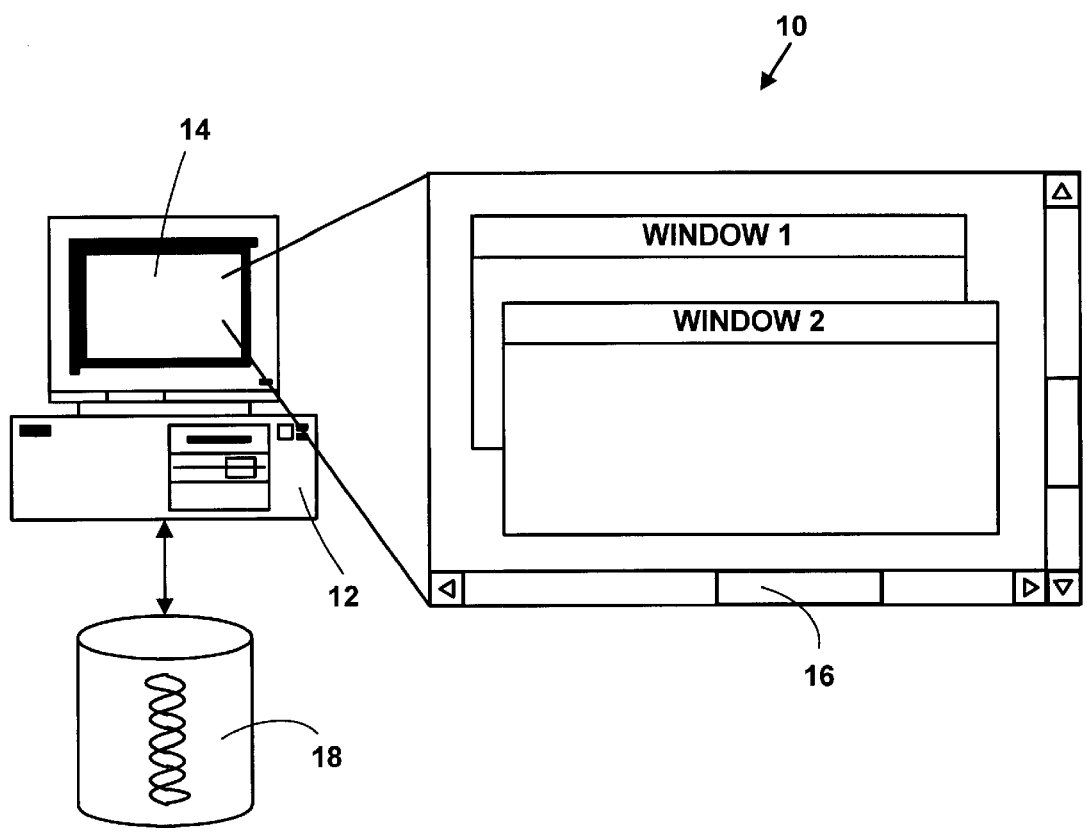
FIG. 1 is a block diagram illustrating an exemplary experimental data processing system.

In one exemplary preferred embodiment of the present invention, biotechnology data for simultaneous sequence-specific identification of expressed genes is processed with the methods and system described herewith. However, the present invention is not limited to processing biotechnology data, and methods and system described herein can be used to process other data (e.g., telecommunications data, electrical data, optical data, physical data, other data, etc.).

Gene Mapping

As was discussed above, deoxyribonucleic acid ("DNA") is a double-stranded heteropolymer that can be thought of symbolically as a continuous string of four nucleotide base elements, deoxyadenosine, deoxycytidine, deoxyguanosine, and deoxythymidine. The four bases are usually abbreviated as "A," "C," "G" and "T" respectively, and base elements on one strand of DNA interact with a counterpart on the other strand. For example, an "A" can only interact with a "T," and a "G" can only interact with a "C." This relationship is called "base pairing."

"Genes" are regions of DNA, and "proteins" are the products of genes. Proteins are built from a fundamental set of amino acids, and DNA carries amino-acid coding information. When DNA is replicated or copied, a new DNA strand is synthesized using each of the original strands as templates.

DNA itself does not act as a template for protein decoding or synthesizing. A complementary copy of one of the two strands of DNA is synthesized out of ribose nucleotides to generate a ribonucleic acid ("RNA") copy of a gene with a method called "transcription." The RNA copy of a gene is then decoded by protein synthesis with a method called "translation." Since the RNA carries protein codes, it is called messenger RNA ("mRNA"). The transcription of mRNA is very precise and always starts at one precise nucleotide and ends exactly at another. Complementary DNA ("cDNA") is an exact, double-stranded DNA copy of mRNA. One of the cDNA strands is complementary to the mRNA, and other is identical.

There are many techniques known in the biotechnology arts to identify RNA species including those described in "Differential display of eukaryotic messenger RNA by means of polymerase chain reaction," by P. Liang and A. B. Pardee, Science, Vol. 257, pages 967–971, 1992; "Arbitrarily primed PCR fingerprinting of RNA," by J. Welsh, K. Chada, S. S. Dalal, R. Cheng, D. Ralph and M. McCelland, Nucleic Acids Research, Vol. 20, pages 4965–4970, 1992; "A simple and very efficient method for generating cDNA libraries," Gene, Vol. 25, pages 263–269, 1983; "Tissue-specific expression of mouse α-amylase genes," by K. Schibler, M. Tosi, A. C. Pittet, L. Fabiani and P. K. Wellauer, Journal of Molecular Biology, Vol. 142, pages 93–116, 1990; "Discovering the secrets of DNA," by P. Friedland and L. H. Kedes, Communications of the Association for Computing Machinery ("CACM"), Vol. 28, No. 11, pages 1164–1186, November 1985; and others.

RNA isolated from a target organism (e.g., a cell to which a new drug has been applied) is analyzed using a method of simultaneous sequence-specific identification of mRNAs. In one preferred embodiment of the present invention, simultaneous sequence-specific identification of mRNAs is provided with a TOtal Gene expression Analysis method ("TOGA"), described in U.S. Pat. No. 5,459,037 and U.S. Pat. No. 5,807,680, incorporated herein by reference. However, other methods can also be used to provide sequence-specific identification of mRNAs, and the present invention is not limited to TOGA sequence-specific identification of mRNAs.

In one preferred embodiment of the present invention, preferably, prior to the application of the TOGA method or other methods, the isolated RNA is enriched to form a starting polyA-containing mRNA population by methods known in the art. In such a preferred embodiment, the TOGA method further comprises an additional Polymerase Chain Reaction ("PCR") step performed using one of four 5' PCR primers and cDNA templates prepared from a population of antisense complementary RNA ("cRNA"). A final PCR step using one of a possible 256 5' PCR primers and a universal 3' PCR primer produces as PCR products, cDNA fragments that corresponded to a 3'-region of the starting mRNA population.

A label (e.g., a dye) is incorporated in the PCR products to permit detection of the PCR products by laser-induced fluorescence. Gel-electrophoresis or equivalent techniques are used to resolve molecules from the PCR products into distinct bands of measurable lengths (See, e.g., FIG. 6). The produced PCR products can be identified by a) an initial 5' sequence comprising a nucleotide base sequence of a remainder of a recognition site or a restriction endonuclease that was used to cut and isolate a 3' region of cDNA reverse transcripts made from a mRNA population, plus the nucleotide base sequence of preferably four parsing bases immediately 3' to the remainder of the restriction enconuclease recognition site, or more preferably the sequence of the entire fragment; and b) the length of the fragment.

Processing PCR product data, including determining a nucleotide base sequence is a very complex task. Whether the TOGA method is used or not, the nucleotide sequences near the end of mRNA molecules give each mRNA an almost unique identity. In addition, data concerning a position and an amplitude of laser-induced fluorescence signals for PCR products are digitized and used to determine the presence and relative concentration of corresponding starting mRNA species. For example, PCR product data is digitized by creating a data file with digital information. The data file may include digital values, for example, of optical brightness of electrophoresis patterns or other data used to identify the mRNA (e.g., data from a micro-array on a chip used to isolate the mRNA). To aid in the detection and analysis of mRNA sequences, a data file including experimental data is processed. In one exemplary preferred embodiment of the present invention, an experimental data processing system is used to process experimental data.

In one preferred embodiment of the present invention, the experimental data includes polynucleotide data for DNA, cDNA, cRNA, mRNA, or other polynucleotides. The polynucleotide data can include, but is not limited to, a length of a nucleotide fragment, a base composition of a nucleotide fragment, a base sequence of a nucleotide fragment, an intensity of a dye label signal used to tag a nucleotide fragment, or other nucleotide data. However, tie present invention is not limited to polynucleotide data and other experimental data can also be used.

Exemplary Experimental Data Processing System

FIG. 1 is a block diagram illustrating an exemplary experimental data processing system 10 for one exemplary preferred embodiment of the present invention. The experimental data processing system 10 includes a computer 12 with a computer display 14. The computer display 14 presents a windowed graphical user interface ("GUI") 16 to a user. A database 18 includes biotechnology experimental information or other experimental information. The database 18 may be integral to a memory system on the computer 12 or in secondary storage such as a hard disk, floppy disk, optical disk, or other non-volatile mass storage devices.

An operating environment for the data processing system 10 for preferred embodiments of the present invention include a processing system with one or more speed Central Processing Unit(s) ("CPU") and a memory. The CPU may be electrical or biological. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed" or "CPU executed."

It will be appreciated that acts and symbolically represented operations or instructions include the manipulation of electrical signals or biological signals by the CPU. An electrical system or biological system represents data bits which cause a resulting transformation or reduction of the electrical signals or biological signals, and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or nonvolatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

Analyzing Biotechnology Data

In one exemplary preferred embodiment of the present invention, a label is incorporated in target biotechnology products (e.g., polynucleotide PCR products) for detection by laser-induced fluorescence and electrophoresis is used to obtain biotechnology data. However, other techniques may also be used to collect experimental biotechnology data (e.g., micro-arrays).

A complex, multi-component information signal based on an indicated fluorescence intensities of the biotechnology products is included in a resulting experimental data file as digital data. The multi-component information signal includes raw multi-component label fluorescence intensities. Label responses are relatively broadband spectrally and typically include spectral overlap. Energy measured as a second fluorescence response typically includes energy in the tail of a first fluorescence response, which might also be present, and vice-versa.

This spectral overlap needs to be removed because the relative quantities of commingled energy may be of a same order of magnitude as relative fluorescence responses of the data representing target data (e.g., polynucleotide data). For example, a small fluorescence response for a given polynucleotide data fragment in a biotechnology product may be "overwhelmed" if it occurs in a spectral overlap region between two fluorescence responses. In an exemplary preferred embodiment of the present invention, spectral overlap is removed and a normalized baseline is created with a combination of filtering techniques.

Removing Spectral Overlap and Normalizing Data

FIG. 2 is a flow diagram illustrating a Method 20 for data normalization of a multi-component data signal. At Step 22, a multi-component data signal is read. The multi-component data signal includes multiple individual data signal components of varying spectral characteristics with varying amplitudes. The multiple individual data signal components overlap within portions of the multi-component data signal. At Step 24, a spectral filter is applied to the multi-component data signal to create multiple non-overlapping individual data signal components. At Step 26, a spatial filter is applied to multiple signal artifacts in the multi-component data signal that introduce ambiguity to base values in the multiple non-overlapping individual data signal components to spatially detrend and normalize the multiple non-overlapping individual data signal components to a uniform base value.

In one preferred embodiment of the present invention, the spectral characteristics of the multi-component data signal comprise physical attributes and conditions including but not limited to, an absorption spectrum of a dye label, an emission spectrum of a dye label, an emission wavelength power and pulse duration of an exciting laser, or other spectral characteristics. The spectral filtering at Step 24 of Method 20 includes "demultiplexing" or separating individual components of raw fluorescence intensities that are combined by overlap of spectral characteristics of different dyes used to tag polynucleotide data (e.g., mRNA, cDNA, or DNA). Polynucleotide data or other data tagged with a dye is called "dye taggant." However, Method 20 is not limited to processing fluorescence intensities from polynucleotide data and can be used to process other types of data that generate a multi-component data signal.

In one exemplary preferred embodiment of the present invention, spectral filtering makes use of a set of coefficients that represent a relative degree to which energy in fluorescence responses of various dye taggants overlap. Denoting this set of coefficients by $\{m(p,q)\}$, $m(p,q)$ is a measurement of an amount of energy measured at a wavelength that corresponds to a center of a fluorescence response of a p-th dye taggant, which is actually due to fluorescence response of a q-th dye taggant at that wavelength. The total unfiltered fluorescence response measured at any such central wavelength is then taken to be a weighted sum of the actual dye-specific fluorescence response. An unfiltered, measured fluorescence intensity at the central wavelength of the p-th dye taggant is denoted as $A'(p)$ and an actual dye-specific fluorescence intensity is denoted as $A(q)$. In terms of these conventions, Equation 1 illustrates a relationship between measured and actual fluorescence intensities.

$$A'(p)=\Sigma_q m(p,q)A(q) \qquad (1)$$

The spectral filter comprises extracting the actual fluorescence intensity $A(q)$, by inverting a linear system of equations in Equation 1 using a singular value decomposition of a coefficient matrix $m(p,q)$. The spectral overlap coefficients $m(p,q)$ and unfiltered fluorescence intensity $A'(p)$ are typically obtained from measurements as part of the calibration of instrumentation used to produce and record the fluorescence intensities. However, these values can also be obtained from other sources. This extraction is an exemplary spectral filter used at Step 24 of Method 20. However, other spectral filters could also be used and the present invention is not limited to the spectral filters illustrated by the inversion of Equation 1.

The spectral filter is followed by a spatial filter at Step 26 of Method 20. In one exemplary preferred embodiment of the present invention, the spatial filter is a nonlinear morphological gray-scale "rolling ball" transformation, which spatially detrends and normalizes the intensities to a set of uniform base line values. However, other types of spatial filters could also be used and the present invention is not limited to the spatial filters described herein.

In one exemplary preferred embodiment of the present invention, the nonlinear morphological gray-scale rolling ball transformation that spatially "detrends" and "normalizes" the fluorescence intensity traces to a set of uniform base line values has two stages. The first stage creates a version of a trace that excludes local variations whose spatial extent is below a certain scale. This scale is chosen to be slightly greater than a measured extent along a trace of typical standard data peaks, so a resulting trace very closely resembles an original trace with peaked regions on a spatial scale of standard peaks and smaller peaks smoothed away. In preferred embodiments of the present invention, data peaks include entities having at least two dimensions characterized by a maximum amplitude and a width. The data peaks may also be described by a width at a half-maximum amplitude or a position of a maximum amplitude.

This inherently nonlinear process is followed in a second stage by forming a difference between an original and a smoothed version of the trace, leaving a uniformly base-lined residual including peaked regions on a spatial scale of standard peaks and smaller. The term "rolling ball" refers to how the smoothed version of a trace is formed in a first stage of this filtering. In effect, a "ball" of a radius set by a exclusion scale of interest is first "rolled" along an under side of a trace, while maintaining at least one point of contact with the trace. A new trace is formed by taking, at each sample index (e.g., a scan line), a highest point of the ball when its center is on a sample index. This is followed by a pass of the same ball along the top side of this new trace, with a final new trace formed by taking, at each sample index, the lowest point of the ball when its center is on the sample index.

If f(n) is a fluorescence intensity of a trace measured at sample index n, $f_{min}$ is set equal to a minimum fluorescence intensity across an entire trace. A spatial scale of standard peak features is taken to be slightly less than N-sample indices (e.g., N-scan lines). The trace is first "eroded" by forming a new trace f_(n) as illustrated in Equation 2.

$$f\_(n) = \min\{f(n+m) - f_{min} : -N/2 \leq m \leq N/2\} \quad (2)$$

The eroded trace f_(n) from Equation 2 is "dilated" as illustrated in Equation 3.

$$f_\pm(n) = \max\{f\_(n+m) + f_{min} : -N/2 \leq m \leq N/2\} \quad (3)$$

A fluorescence intensity of the rolling ball filtered version of an original trace at sample index n is $f_0(n)$ as is illustrated in Equation 4.

$$f_0(n) = f\_(n) - f_\pm(n) \quad (4)$$

It is a sequence of finding minima and maxima (e.g., Equations 3 and 4) that accounts for the nonlinearility of the filter. Data values are normalized to a set of uniform base values.

The present invention with Method 20 is not limited to processing and normalizing biotechnology data multi-component signal or processing data with Equations 1–4 and can be used for other data from a multi-component signal (e.g., telecommunications signals, electrical signals data for electrical devices, optical signals, physical signals, or other data signals).

In one exemplary preferred embodiment of the present invention, "control" or "standard" polynucleotide data fragments (i.e., known polynucleotide data fragments) are tagged with a dye, which under laser illumination responds with a "red" fluorescence, while "target" polynucleotide data fragments (i.e., polynucleotide data to be identified) are tagged with a dye which has a "blue" response. However, the dyes used for the control and target could also be interchanged. Both the red and blue dye responses are relatively broadband spectrally, to the extent that energy measured as red fluorescence response includes energy in a tail of any blue fluorescence response which might also be present and vice-versa. This spectral overlap is taken into account because the relative quantities of commingled energy are of the order of the relative fluorescence intensities of the target polynucleotide data and standard polynucleotide data fragments.

Figure 3B:
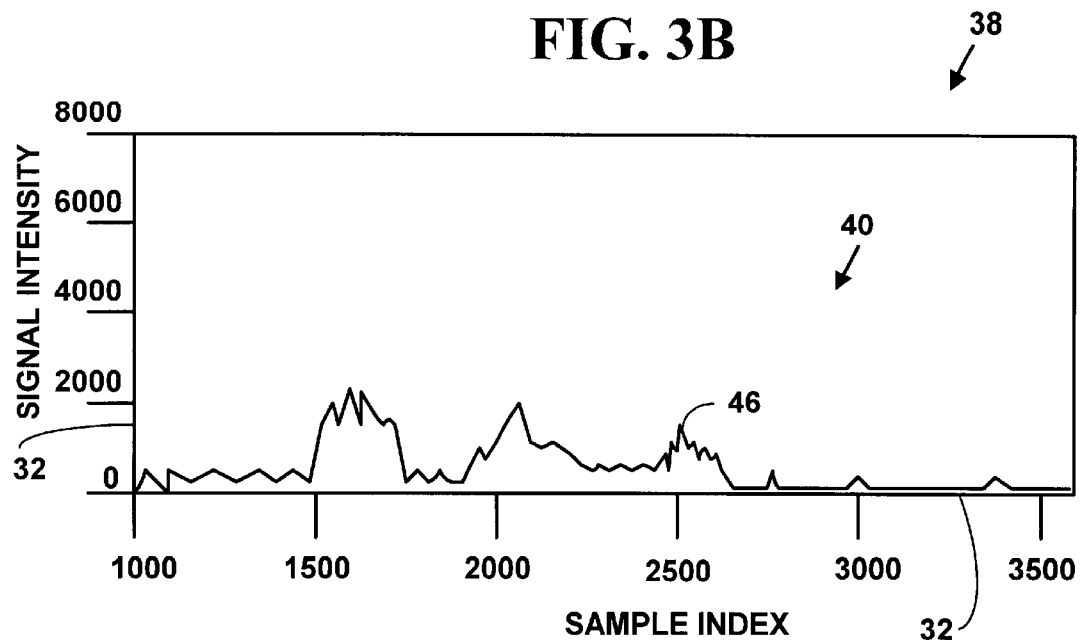
FIG. 3B is a block diagram illustrating the unfiltered multi-component data signal of FIG. 3A as an unfiltered multi-component data signal displayed with a larger scale.

FIG. 3A is a block diagram 28 of an unfiltered multi-component data signal 30. FIGS. 3A–3D are used to illustrate use of Method 20 of FIG. 2. In one exemplary preferred embodiment of the present invention, the multi-component data signal 30 is a measurement of signal intensity of fluorescence on a vertical axis 32 at a fixed point in an electrophoresis-gel at successive points in time. The signal intensity of fluorescence is directly proportional to a parameter on a horizontal axis 34 representing a sample index (e.g., a scan line). However, other multi-component signal data could also be used and the present invention is not limited to polynucleotide fluorescence intensity data. A magnitude of the fluorescence intensity at a given scan line has been demonstrated to represent an amount of tagged polynucleotide fragments at a fixed point in time of a scan (e.g., tagged with red or blue dyes). The scale of standard polynucleotide fragment fluorescence intensity is illustrated by the narrow peak 36, of about two-hundred fluorescence units, which is illustrated in the region near sample index 2500 (e.g., 2500 scan lines) on the horizontal axis 34. In one preferred embodiment of the present invention, FIG. 3A illustrates a multi-component data signal 30 for a standard set of polynucleotide fragments.

Figure 3C:
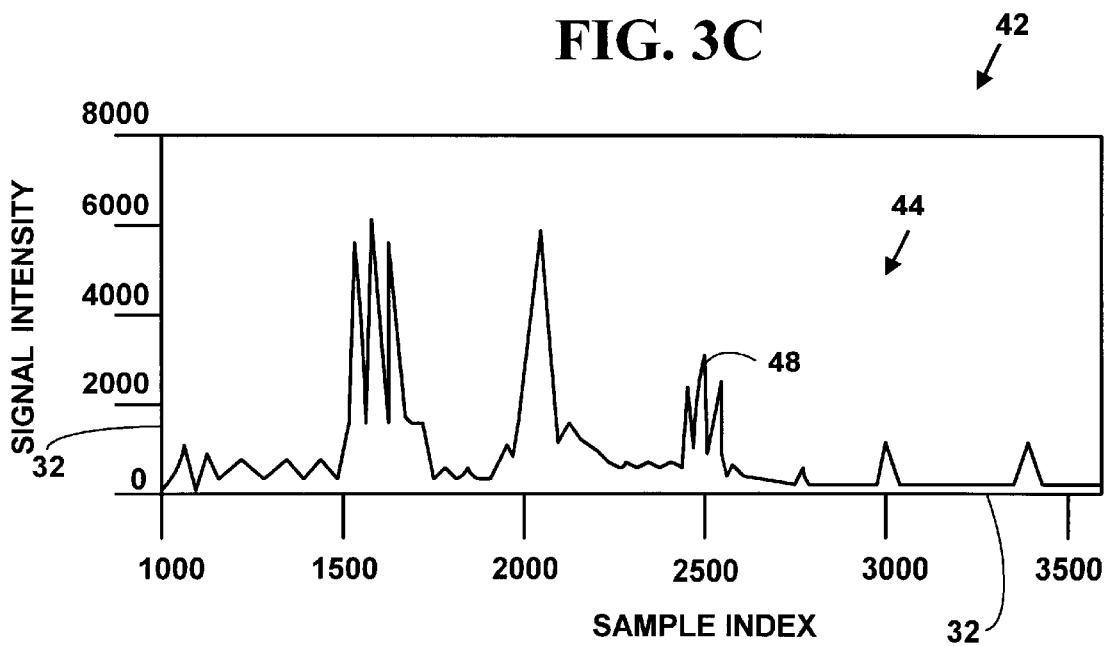
FIG. 3C is a block diagram illustrating a filtered version of the multi-component data signal of FIG. 3A.

FIG. 3B is a block diagram 38 illustrating the unfiltered multi-component data signal 30 for a standard set of polynucleotides fragments of FIG. 3A as an unfiltered multi-component data signal 40 displayed with a larger scale. FIG. 3C is a block diagram 42 illustrating a filtered version of a multi-component data signal 44 for a target set of polynucleotides. The filtered version of the multi-component data signal 44 for the target set of polynucleotides (FIG. 3C) is at least an order of magnitude greater than that of the unfiltered multi-component data signal 40 for a standard set of polynucleotides (FIG. 3B).

A degree of spectral overlap is illustrated by the presence, in the unfiltered multi-component data signal 40 for a standard set of polynucleotides of FIG. 3B, of such artifacts as the broad peaks 46 in the region of sample index 2500 (e.g., 2500 scan lines) on the horizontal axis 32. The broad peaks 46 of FIG. 3B, when compared with the narrower peaks 48 of FIG. 3C, are due to spectral overlap of blue fluorescence intensities from blue-tagged target polynucleotide fragments since there are no red-tagged standard polynucleotide fragments that could produce such levels of fluorescence intensities. An ambiguous baseline in this region (i.e., 2500 scan lines) illustrates "spectral bleed through" of blue-tagged target polynucleotide fragments that dramatically dwarf red-tagged standard polynucleotide fragments of interest.

FIG. 3D is a block diagram 52 illustrating application of Method 20 of FIG. 2 to the unfiltered multi-component data signal 30 for the standard set of polynucleotide fragments of FIG. 3A. FIGS. 3A and 3D use the same signal intensity scale to allow direct comparison. Note the clean data peaks 54, 56, 58, 60, 62, 64, 66, 68, 70 and 72 in FIG. 3D normalized to a uniform base value by applying the spectral and spatial filters of Method 20 to the unfiltered multi-component data signal 30 for the standard set polynucleotide fragments of FIG. 3A. Method 20 of FIG. 2 is also applied to the multi-component data signal for the target set of polynucleotides of FIG. 3B to produce set of clean peaks similar to those in FIG. 3D (this is not illustrated in FIG. 3).

Standards Size Data Detection, Error Removal and Clutter Rejection

The multi-component data signals filtered and normalized to a baseline value with Method 20 of FIG. 2 may still contain false or erroneous data peaks due to false peak clutter. Such erroneous or false data peaks, if not removed, may skew experimental results. In one exemplary preferred embodiment of the present invention, size standards detection with removal of false peak clutter rejection is used to identify a set of valid biotechnology fragment data from a filtered set of biotechnology fragment data (e.g., polynucleotide data). However, size standards detection with removal of false peak clutter can also be used on data other than biotechnology fragment data.

FIG. 4 is a flow diagram illustrating a Method 74 of clutter rejection. At Step 76, a first set of data points is selected from a filtered set of data points (e.g., filtered using Method 20, FIG. 2) using initial threshold criterion. At Step 78, multiple overlapping subsets of data points are selected from the first set of data points. At Step 80, multiple linear mappings are applied to the multiple overlapping subsets of data points. At Step 82, multiple error values are determined from the application of the multiple linear mappings to the multiple overlapping sub-set of data points. At Step 84, a first final subset of overlapping data points with a smallest error value is selected from the first set data points. Data points in the first final subset of overlapping data points include data points that fall within a standardized range where false data points have been removed.

In one exemplary preferred embodiment of the present invention, peaks in candidate biotechnology fragment data are located at Step 76 (FIG. 4) in filtered biotechnology fluorescence intensity data (e.g., with Method 20) using thresholds on simple ratios of differences between "microscale" and "mesoscale" average fluorescence intensity levels relative to mesoscale variances. However, other thresholds could also be used.

There are typically a very large number of sets of filtered data points that can be selected for use with Method 74. Thus, selecting an appropriate filtered set of data points is a "combinatorics" problem. As was discussed above, combinatorics relates to the arrangement of, operation on, and selection of discrete elements belonging to finite sets of data points. However, Method 74 reduces the combinatorics of data selection to a "best" possible solution using multiple linear mappings, and allows a best set of data points (e.g. for a data peak mapping) to be created from a very large set of filtered data points. Method 74 provides an accurate selection of data points on data sub-scale, instead of a electrophoresis-gel scale, thus reducing the combinatorics of data selection to a level usable on the current generation of computing systems.

In one exemplary preferred embodiment of the present invention, a "signal-to-noise" ratio combined with a "height-and-width" ratio is used at Step 76. However, other initial thresholds can also be used, and the present invention is not limited to the initial threshold wherein described. The initial threshold is used in one exemplary preferred embodiment of the present invention as an initial threshold overview to identify a likely set of false standard biotechnology fragment peak features (e.g., in polynucleotide fragments). Data outside the initial threshold is rejected as is illustrated in FIG. 5 below. An actual sample index location of a given candidate is taken to be that of a local maximum of a peak feature, if this is unique, or alternatively to a spatial center of a feature interval.

FIG. 5 is a block diagram 86 illustrating a filtered and normalized multi-component data signal using Method 20 from FIG. 2. To illustrate the difficulty in size standard detection for polynucleotide data fragments, FIG. 5 illustrates a relatively clean set of superficially acceptable data peaks. However, there are features 88 and 90 near sample indices 1400 and 3250, which may satisfy a signal-to-noise criterion but fail a height-and-width criterion used to determine a data peak (Items 88 and 90 of FIG. 5 correspond to items 98 and 100 of FIG. 6). The features 88 and 90 are rejected with the initial criterion at Step 76. However, there are also features 92 and 94 near sample index 2700 that meet the initial criterion, but which are not valid standard peaks for this exemplary biotechnology data trace (items 92 and 94 of FIG. 5 correspond to item 102 of FIG. 6). These features 92, 94 are removed with the remainder of Method 74 at Steps 78–84. It is desirable to consistently remove such invalid peaks to create a valid set of standard peaks (e.g., for polynucleotide data fragments), to allow reproducible results every time an experiment is conducted.

In one exemplary preferred embodiment of the present invention, modeling physics of gel electrophoresis used to record polynucleotide data fragments is done using Fickian diffusion with drift. However, other modeling techniques could also be used and the present invention is not limited to Fickian diffusion with drift. As is known in the art, Fickian diffusion is molecular diffusion, governed by Fick's laws, which describe a rate of flow of diffusants across a unit area of a certain plane as directly proportional to a concentration gradient. For more information on Fickian diffusion see "Diffusion Processes and Their Sample Paths" by Henry P. McKean and Kiyoshi Ito, Springer Verlag, 1996, ISBN-3540606297, or "Mathematics of Diffusion" by John Crank, Oxford University Press, 1975, ISBN-0198534116, both of which incorporated herein by reference.

Using Fickian diffusion on a gel, the drift properties of diffusants are associated with the times of arrival of their maximum concentrations at a fixed point in a gel. For linear molecules of interest, this arrangement leads to at least three significant model predictions for polynucleotide data fragments. First, the polynucleotide data fragments drift with velocity inversely proportional to their size. Second, for sparse mixtures, fluorescence peak heights are proportional to polynucleotide data fragment counts. Finally, both of these proportionalities are independent of polynucleotide data fragment size. The value of gel electrophoresis in biomolecular size assays is due to the fact that it is possible to engineer instruments and protocols for which these predictions are valid for a significant variety of conditions and molecules.

In one exemplary preferred embodiment of the present invention, comigrating standard polynucleotide fragment sets of known size provide a means of rejecting the false peak clutter. Since an inverse proportionality between fragment size and drift velocity is independent of fragment size, and a standard fragment set is both known and ordered, a straight line drawn through a plot of standard fragment sizes as a function of their scan line locations should reveal those data peaks that are clutter. The clutter peaks will either not fall on, or sufficiently near a line, or they will cause a line to miss a significant fraction of the other data.

Given this approach to clutter rejection, there are at least two remaining problems in applying it to biotechnology data. First, potential combinatorics of quickly choosing an appropriate subset of valid peaks from candidate peaks can be computationally impossible or forbidding for currently available computing systems. Secondly, a degree to which an inverse proportionality of fragment and drift velocity size is genuinely independent of fragment size depends upon a degree to which gel properties are consistent and uniform over a period of observation.

Figure 6:
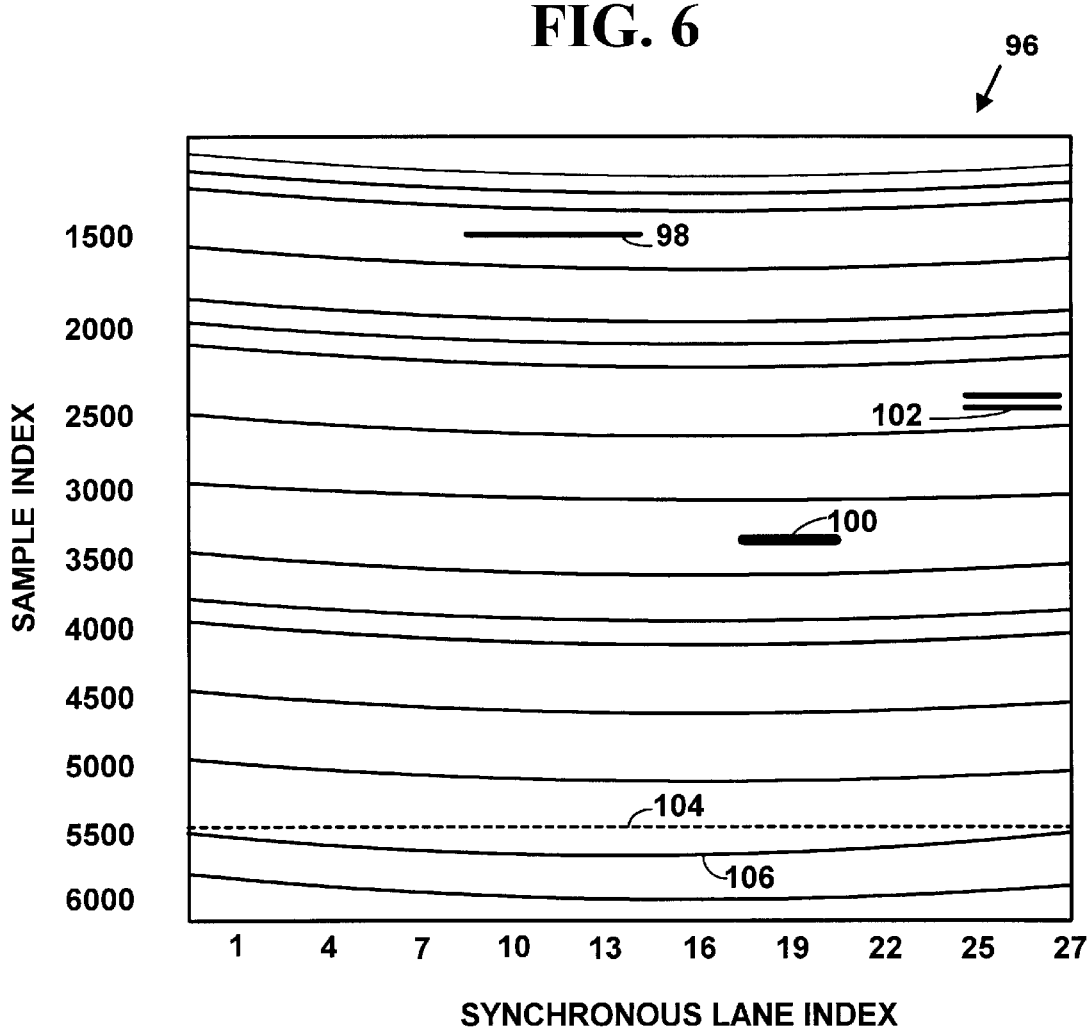
FIG. 6 is a block diagram illustrating a filtered standard for a sequence of scans for a set of lanes in an electrophoresis-gel that were loaded with standard polynucleotide fragments at the same time.

FIG. 6 is a block diagram 96 illustrating filtered standard polynucleotide fluorescence responses for a sequence of scans for a set of lanes in a gel which were loaded with standard polynucleotide fragments at a same time. The physical edges of the gel correspond to the edges of this image, and the bright bands in any one lane represent the scan line locations of candidate standard fragments in that lane. For example, the three scan lines near sample index 2000 (FIG. 6) represent the three data peaks near sample index 2000 (FIG. 5). Note the smaller bright features 98, 100 and 102, roughly in the center of lanes 10, 19, and 25, that do not belong to bands that extend across the image. These are examples of the "false peak clutter" at issue. For example, item 98 (FIG. 6) may correspond to false peak 88 (FIG. 5), item 100 may correspond to false peak 90 (FIG. 6) and item 102 (FIG. 6) may correspond to false peaks 92, 94 (FIG. 5).

If the properties of the gel were uniform throughout the gel over a period of successive scans, the bright bands would be strictly horizontal (e.g., exemplary horizontal dashed line 104). Not only are the bands not horizontal, the degree to which they curve increases as a function of time, with larger scan lines indices corresponding to scans occurring later in time. The drifting fragments in the gel are charged particles moving through a resistive medium under the influence of an applied electric field. The resulting characteristic "smile" (e.g., scan line 106 versus horizontal line 104) in such electrophoretic gel imagery is due to the differential heating of the gel by this current over time, the edges of the gel more effectively dissipating heat than the more central regions.

The smaller a linearly ordered set of standard fragment sizes (e.g., a mask) is, the more the resulting combinatorics of selecting a valid subset (e.g., flickering a mask) become tractable. For overlapping regions of the gel to which each mask is applied, the more uniform and consistent the relevant gel properties become localized.

In one exemplary preferred embodiment of the present invention, a given set of candidate standard peak scan line locations are obtained at Step 76 by the initial threshold criterion outlined above. In such an embodiment, clutter and false peak rejection proceeds by choosing proper, overlapping subsets of a complete standard size set at Step 78.

At Step 78, linear mappings are applied to the multiple overlapping subsets of data points. For an ordered, sequential three element set of standard sizes $\{M_a, M_b, M_c\}$ whose peaks occur at scan lines $\{n_a, H_b, n_c\}$, respectively, linear regression techniques give a predictive linear mapping of scan line $n_x$ to fragment size as is illustrated in Equation 5. However, other set sizes and linear mappings could also be used and the present invention is not limited to the linear mappings in Equation 5.

$$\mu^{(0)}_{abc} + \mu^{(1)}_{abc} * n_x, \quad (5)$$

The coefficients $\{\mu^{(j)}_{abc}\}$ are functions of a particular set of (size, scan line) pairs. With any scan line n lying between two consecutive standard peak scan line locations, $\{n_b, n_c\}$, a local Southern linear mapping method associates a fragment size as is illustrated in Equation 6. However, other linear mapping methods can also be used, and the present invention is not limited to the local Southern method linear mappings illustrated in Equation 6.

$$M'_n \equiv (\mu^{(0)}_{abc} + \mu^{(1)}_{abc} * n + \mu^{(0)}_{bcd} + \mu^{(1)}_{bcd} * n)/2 \quad (6)$$

The set $\{M_b, M_c, M_d\}$ is a rightmost overlapping "bcd" and sequential set of standard sizes for a leftmost overlapping "abc" and sequential set $\{M_a, M_b, M_c\}$, the former for standard size peaks occurring at scan lines $\{n_b, n_c, n_d\}$. An individual error in this association of standard peak size (i.e., data point value) and scan line location (i.e., data point) is calculated as a difference illustrated by Equation 7.

$$\epsilon_n \equiv M_n - M'_n \quad (7)$$

At Step 82, multiple error values (e.g., Equation 7) are determined from the application of multiple linear mappings (e.g., Equation 6) to the multiple overlapping subset of data points. In one preferred embodiment of the present invention, a Root Mean Square ("RMS") error evaluation of the "goodness" of each of the local fits allows them to be ranked. However, other error evaluation methods can also be used and the present invention is not limited to RMS.

Given a set of peak scan line locations for a set of standard biotechnology fragments sizes, straight lines are fit to possible sets of three adjacent fragment sizes as a function of the three associated adjacent scan line locations, using linear regression. A local linear mapping of any given scan line to its associated fragment size is then formed by averaging the two most relevant of these three-point linear fits.

A first relevant fit includes two closest standard scan lines, which are smaller than a given scan line, and one closest standard scan line, which is greater. A second relevant fit includes two closest standard scan lines, which are greater than a given scan line, and one closest standard scan line which is smaller. A total RMS error over the K (size, scan line) pairs $\{(M_{n(k)}, n(k))\}$ is illustrated in Equation 8.

$$\text{error} = [\Sigma_{k=1,\ldots,K} \epsilon^2_{n(k)}/K]^{1/2} = [\Sigma_{k=1,\ldots,K}(M_{n(k)} - M'_{n(k)})^2/K]^{1/2} \quad (8)$$

A set of subsets of scan line locations which yields a smallest total RMS error is chosen at Step 84, provided that both a total error and an error for any one standard size are below certain error thresholds. If these error thresholds cannot be satisfied by any subset of scan line locations for a complete set of standard sizes, a size of a standard size set is reduced by one and the error calculation is repeated. This method of evaluating local linear fits to possible subsets of standard scan line locations is repeated, over possible standard size sets of the reduced size. The RMS process (e.g., Equation 8) is repeated until either error threshold criterion are satisfied, or until a reduced size of the standard size set becomes too small. There is also a selection criterion on the subsets of the complete standard size set that prevents more than a given number of adjacent lacunae in final size set.

FIG. 7 is a block diagram 108 illustrating exemplary biotechnology peaks (e.g., polynucleotide peaks) using size standard detection with false peak clutter rejection from Method 74 of FIG. 4. Target biotechnology fragment peaks 110, 112, 114, 116, 118, 120, 122, 124, 126 and 128 identified by Method 80 (FIG. 4) while standard biotechnology peaks (e.g., sample indices for known polynucleotide data sequences) are indicated by with dashed vertical lines. For example, the dashed line through the data peak 110 indicates a known polynucleotide intensity. The false peaks 88, 90 (FIG. 5) near scan lines 1400 and 3250 that may satisfy a signal-to-noise criterion but fail a height-and-width criterion are properly identified and removed with initial criterion at Step 76 of Method 80. The false peaks 92, 94 (FIG. 5) have been properly identified and rejected as clutter by the remaining steps of Method 80. Note that several of the data peaks (e.g., 114, 118, 122) for target data do no line up exactly on a dashed line for known data. Such data peaks are adjusted as is described below.

Method 74 (FIG. 4) may also allow for the application of a number of very powerful and convenient quality control measures. First, Method 74 may implicitly bootstrap a sizing calibration. This allows a quality of fluorescence intensity data to be immediately assessed from their susceptibility to accurate calibration. This may be an effective measure of the degree of conformance between experimental data and a good physical model of the processes implicated in their creation. Secondly, limits are placed on both the total number and distribution of size standards fragments that can be deleted from the initial set in producing a set of local linear mappings with acceptable error. Finally, it is assumed that false peak clutter usually has its source in either residual spectral bleed-through, or more problematically for any given lane, standard fragment sets which actually belong to adjacent lanes. This latter phenomenon is known as "crosstalk." By keeping track of both how many candidate standard peak scan line locations co-occur in adjacent lanes as well as how many detected standard peaks are co-located in adjacent lanes even after application Method 74, it is possible to form yet another useful data quality measure. This measure may be particularly relevant to clutter rejection because it essentially qualifies its self-consistency.

Data Size Calibration and Adjustment

The actual size and location of the filtered and false peak clutter rejected data (e.g., polynucleotide fragment output) is typically adjusted to allow experimental data to be more accurately visually displayed. This adjustment provides more accurate data values for visual display. For example, target data peaks illustrated in FIG. 7 that do not line up exactly on a known data peak values are adjusted.

FIG. 8 is a block diagram illustrating a Method 130 for data size calibration and adjustment. At Step 132, a first final subset of overlapping data points with a smallest error value is selected as a standard set of data points from a first set of data points. Data points in the first final subset of overlapping data points include data points with values that fall within a standardized range and where false data points have been removed. At Step 134, higher order mappings are applied to the first final subset of data points to further reduce the smallest error value for the final subset of overlapping data points and create a second final subset of data points.

In one preferred embodiment of the present invention, a first subset of overlapping data points is selected at Step 132 from application of Method 74 (FIG. 4). However, other methods can also be used to select the final subset of overlapping data points, and the present invention is not limited to the application of Method 74.

At Step 132, the first final subset of overlapping data points selected from application of Method 74 including a local Southern method (e.g., Equations 5 and 6), size-calibrates data with a pre-determined precision (e.g. typically no better than one to two base pairs for polynucleotide fragment data). If the data points can be calibrated in Step 132 to within a pre-determined quality control limit, the local Southern calibration is followed by a higher order mapping at Step 134 that further reduces a calibration error. In one exemplary preferred embodiment of the present invention, the calibration error is reduced to zero. In another exemplary preferred embodiment of the present invention, the calibration error is reduced to a very small value approaching zero, but not to zero (i.e., slightly greater than zero).

Method 130 combines the local statistical robustness of regression techniques (i.e., with their natural rejection of outliers) and a precision possible with higher order methods (e.g., higher order splines). In one exemplary preferred embodiment of the present invention, absolute precision in the calibration biotechnology data is desired to provide accurate and reproducible results. However, the present invention can also be used if only relative precision is desired.

At Step 134, higher order mappings are used with the residual error from the local Southern Method, and a second-order generalization of that linear, or first-order local Southern Method. In one exemplary preferred embodiment of the present invention, local quadratic or second-order maps are constructed using residual errors for the same three element sets of (fragment size, scan line location) pairs used for the Local Southern Method. However, the present invention is not limited to second order maps and higher order maps can also be used (e.g., third order, fourth order, etc.).

Since a second-order mapping has three coefficients, or three "degrees of freedom," the three residual errors for each set of three pairs can in principal, be accounted for in a very exact manner. Computational degeneracy in a numerical order of an error is accomplished by using a singular value decomposition to solve a linear system of equations that a conventional least squares method produces when fitting a quadratic to three data points.

Given the local Southern approximation of a size associated with any specific scan line location, an additive correction higher order mapping is formed by averaging two most relevant of these second three-point quadratic fits. A first approximation, for two closest standard scan lines which are smaller than a given scan line and one closest standard scan line which is greater. A second approximation for two closest standard scan lines which are greater than a given scan line and one closest standard scan line which is smaller. Since each quadratic fit is locally exact at the scan line locations of relevant three standard fragment peaks, averaging any two fits on these peak locations is also exact, which results in an absolutely precise interpolation on the detected standard fragment set.

For a scan line n, the local Southern method (e.g., Equations 5 and 6) associates a fragment size $M'_n$, with error $\epsilon_n$ at the standard peak locations. With the same notation and conventions used for the discussion of the local Southern method above, a least squares method gives exact second order mappings of an error at any one standard peak location for leftmost sequential set of standard sizes as illustrated in Equation 9. However, other methods can also be used and the present invention is not limited to a least squares methods.

$$\gamma^{(0)}_{abc} + \gamma^{(1)}_{abc} * n + \gamma^{(2)}_{abc} * n^2 \tag{9}$$

Exact second order mappings of an error at any one standard peak location for rightmost sequential set of standard sizes is illustrated in Equation 10.

$$\gamma^{(0)}_{bcd} + \gamma^{(1)}_{bcd} * n + \gamma^{(2)}_{bcd} * n^2 \quad (10)$$

Both sets of coefficients $\{\gamma^{(j)}_{abc}\}$ and $\{\gamma^{(j)}_{bcd}\}$ are functions of their respective particular set of (size, scan lines) pairs and the error $\epsilon_n$. For any scan line n lying between two consecutive standard peak scan line locations, $\{n_b, n_c\}$, a higher-order residual mapping adds a correction factor $\delta_n$ to a local Southern method size association as illustrated in Equation 11.

$$\delta_n = (\gamma^{(0)}_{abc} + \gamma^{(1)}_{abc} * n + \gamma^{(2)}_{abc} * n^2 + \gamma^{(0)}_{bcd} + \gamma^{(1)}_{bcd} * n + \gamma^{(2)}_{bcd} * n^2)/2 \quad (11)$$

In one preferred embodiment of the present invention, this correction $\delta_n$, or higher order mapping, gives a net association that is exact at scan line locations of the standard peak features. However, the present invention is not limited to such a correction $\delta_n$ and other correction features could also be used.

Figure 9A:
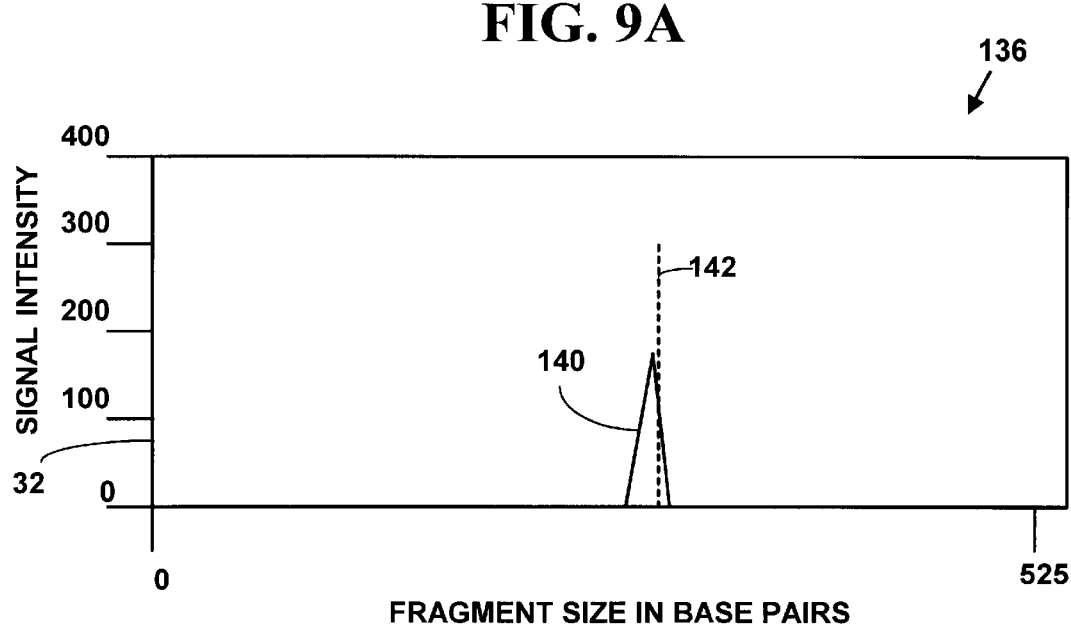
FIGS. 9A and 9B are block diagrams illustrating data size calibration using the method from FIG. 8.
Figure 9B:
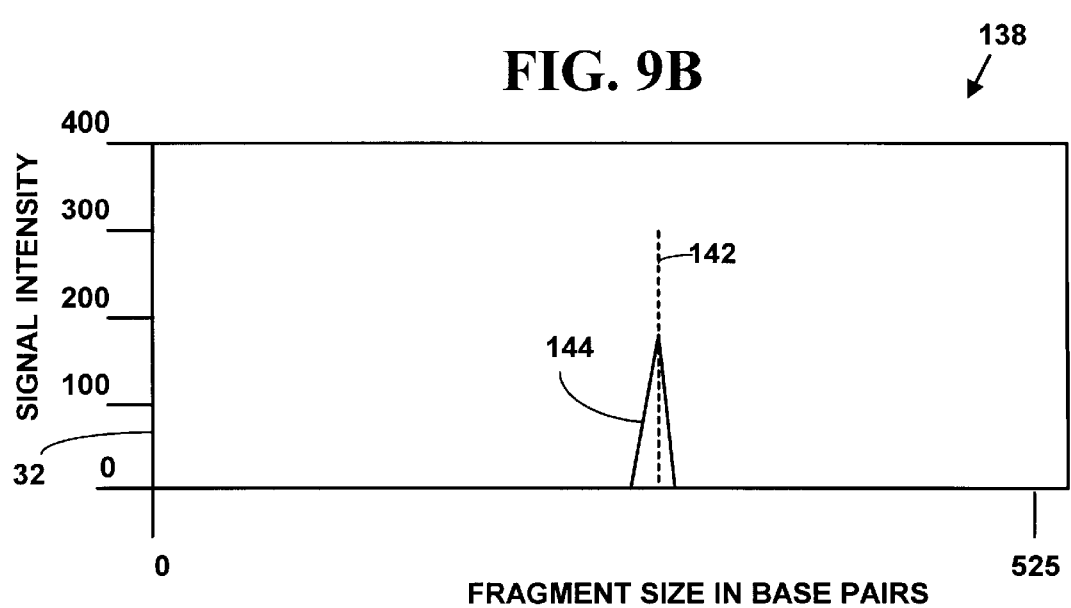

FIGS. 9A and 9B are block diagrams 136, 138 illustrating data size calibration using Method 130 from FIG. 8. FIG. 9A illustrates an exemplary data peak 140 (e.g., for an unknown polynucleotide sequence) before application of Method 130 (FIG. 8). The data peak 140 is slightly offset from a relevant desired data peak location 142 (e.g., for a known polynucleotide sequence) whose desired location is illustrated by a dashed line, that would be achieved if there were no errors for a data set acquired from a desired experiment. FIG. 9B illustrates an exemplary data peak 144 after application of Method 130 (FIG. 8). The data peak 146 is more accurately aligned over the desired data peak location 142 after application of Method 130.

FIGS. 9A and 9B illustrates only one exemplary data peak. However, Method 130 is applied to all data peaks (e.g., 54, 56, 58, 60, 62, 64, 66, 68, 70 and 72 of FIG. 3D) in a final subset of overlapping data points (e.g., produced by Method 74 of FIG. 4) to further reduce error for a set of data points that will be visually displayed. Method 130 may improve a set of data points that will be displayed and analyzed by further reducing data errors that may be introduced as a result of running a desired experiment.

Data peaks that have been sized and adjusted may still include data "stutter." (See e.g., FIG. 11A). For example, the data peaks illustrated in the figures are illustrated as a "smooth" data peaks. However, actual experimental data peaks typically include multiple sub-peaks, that are a function of the actual data. It is desirable to remove the multiple sub-peaks, or data stutter before visual display.

Reduction of Data Magnitude and Data Smoothing

In the current generation of biotechnology equipment known in the art, scan lines from gel-electrophoresis are formed at a rate which, after size calibration, results in an over-resolution of the sized traces by about an order of magnitude. That is, there are about ten scan lines between each successive integer base-pair value. In addition, biotechnology fragments (e.g., polynucleotide fragments) typically occur in cluster around the most significant fragment sizes, rather than as cleanly isolated peaks of integer base-pair width. This can be seen by comparing the broader and more complex peak features (e.g., feature 44) in the biotechnology fragment trace in FIG. 3C, with the narrow and more simple standard fragment peaks in FIG. 3D (e.g., data point 68).

Representing these complex biotechnology fragment traces at their full resolution on the windowed display 16 is further complicated by the inevitable limits imposed by the current generation computer monitor and graphics display systems. Consequently, before creating graphical images to display, the biotechnology data points are further decimated and smoothed using an "envelope detector" that enhances a visibility of data points for display on the windowed display 16 by moderating resulting fragment "stutter."

Figure 10:
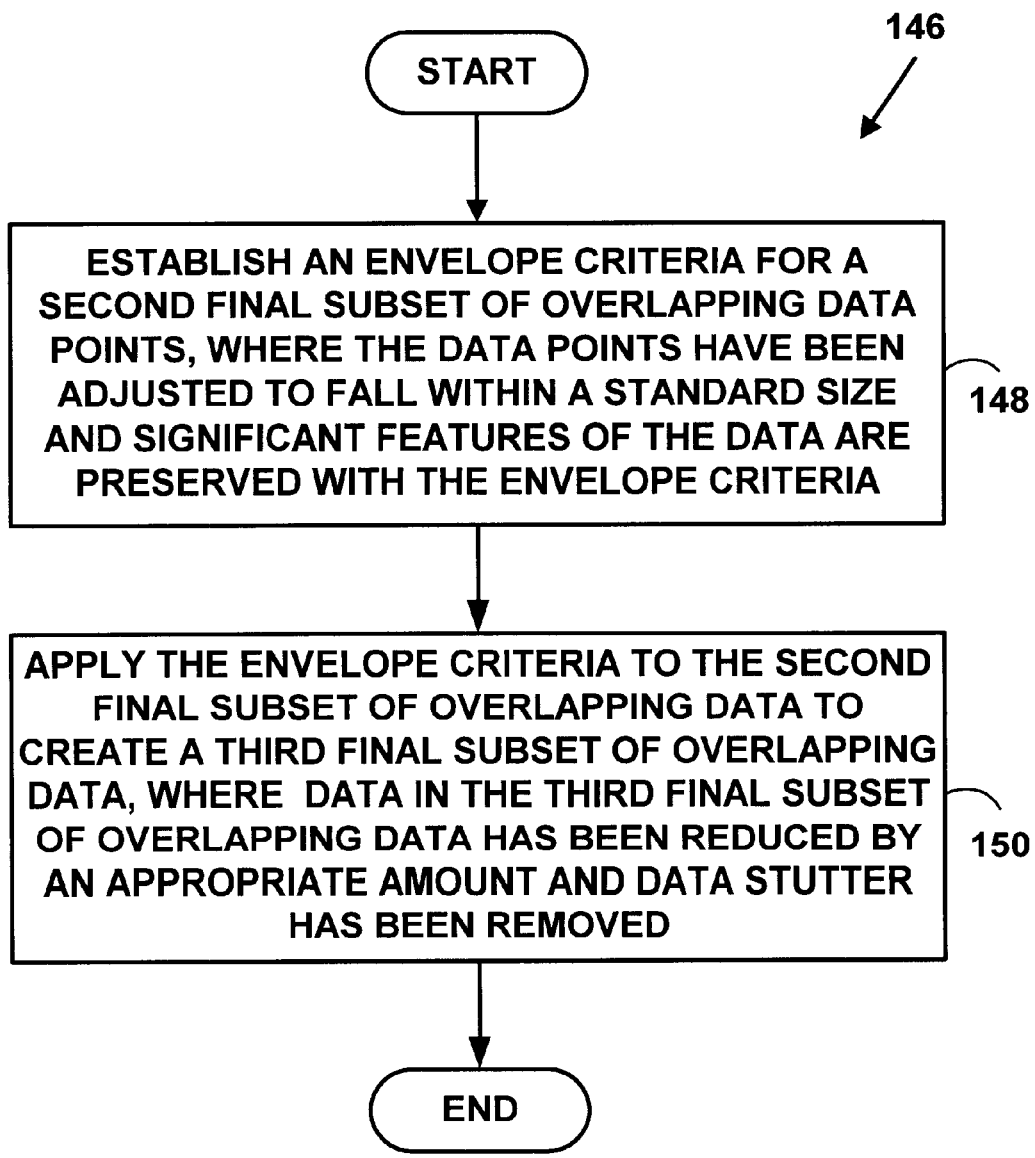
FIG. 10 is a flow diagram illustrating a method for envelope detection.

FIG. 10 is a flow diagram illustrating a Method 146 for envelope detection. At Step 148, an envelope criterion is established for sub-sampling of a second final subset of overlapping data created from a first final subset of overlapping data. The second final subset of overlapping data points have been adjusted to fall within a standard size. Significant features of the second final subset of overlapping data are preserved within the envelope criterion. At Step 150, the envelope criterion is applied to compress the number of data values in the second final subset of overlapping data by at least one order of magnitude, reduce data stutter, and to create a third final subset of overlapping data.

In one exemplary preferred embodiment of the present invention, the second final subset of overlapping data is produced by applying Method 20 (FIG. 2), Method 74 (FIG. 4) and Method 130 (FIG. 8) discussed above. However, the present invention is not limited to overlapping data sets produced with these method and other data sets produced with other methods known in the art, that will be displayed on the windowed display 16 can also be used with Method 146 (FIG. 9).

In one exemplary preferred embodiment of the present invention, the envelope criterion established at Step 148 is based on a "nonlinear box-car-extremum" filter that compresses data size resolution by about an order of magnitude and removes data stutter. However, other envelope criterion could also be used and the present invention is not limited to a nonlinear box-car-extremum filter.

In one preferred embodiment of the present invention, graphical images for the windowed display 16 illustrate a size resolution of about one polynucleotide base pair, with each point on a trace sampled at integer base-pair sizes. At Step 150, the box-car envelope detector first segments a size axis of a size-calibrated full resolution trace data into contiguous regions centered on these integer sizes. The term "box-car" reflects the view of these contiguous, disjoint regions as box-cars aligned end-to-end along a size axis.

A trace envelope is formed by replacing signal intensities associated with sizes in a given box-car by their maximum. This is a many-to-one replacement, or "decimation", on the order of the average number of scan lines associated with an integer base pair in the full resolution data. Preferably, this decimation factor is about ten-to-one. However, other decimation factors can also used.

In one exemplary preferred embodiment of the present invention, at Step 150, an envelope criterion $f^*_k$, is applied in Equation 12.

$$f^*_k = \max\{f_0(n):(M^*_k + M^*_{k-1})/2 \leq (M'_n + \delta_n) < (M^*_{k+1} + M^*_k)/2\} \quad (12)$$

The notation and conventions in Equation 12 reflect notation from Equations 1–11 discussed above. For example, $f_0$ is determined with Equation 4, $M'_n$ with Equation 6, and $\delta_n$ with Equation 11, etc.

FIGS. 11A and 11B are block diagrams 152, 154 illustrating envelope detection using Method 146 of FIG. 10. FIG. 11A illustrates an envelope 156 created around a target data peak 158. Data "stutter" is illustrated by two small peaks on the left side (i.e., towards 2000 sample index), and one small peak on the right side (i.e., towards 2500 sample index) of target data peak 158. FIG. 11B illustrates a new data peak 160 after application of Method 146. The number of data points in the new data peak 160 is reduced by an order of magnitude and the "stutter" of the data peak 158 has been removed. FIGS. 11A and 11B illustrates only one exemplary data peak. However, Method 150 is applied to data peaks in the second final subset of overlapping data. Data peaks described herein, also typically include data "stutter." However, data peaks in other than FIG. 11A are illustrated as smooth and do not illustrate data stutter that does exist before application of Method 146 simplify the drawing of such data peaks.

Method 146 may further enhance a visibility of data points for display on the windowed display 16 by moderating resulting fragment "stutter." The number of data points may also be reduced by an appropriate amount (e.g., one order of magnitude) for easier display.

Processing of General Multi-component Signal Data

In one exemplary preferred embodiment of the present invention, a general multi-component data signal can be processed to yield a set of data peaks for a target experiment suitable for display on the windowed display 16 of the display device 14. In such an embodiment, the general multi-component data signals may include general biotechnology multi-component data signals. However, the present invention is not limited to processing general biotechnology multi-component signal data, and other signal data could also be processed (telecommunications signals, electrical signals data for electrical devices, optical signals, physical signals, or other data signals).

Figure 12B:
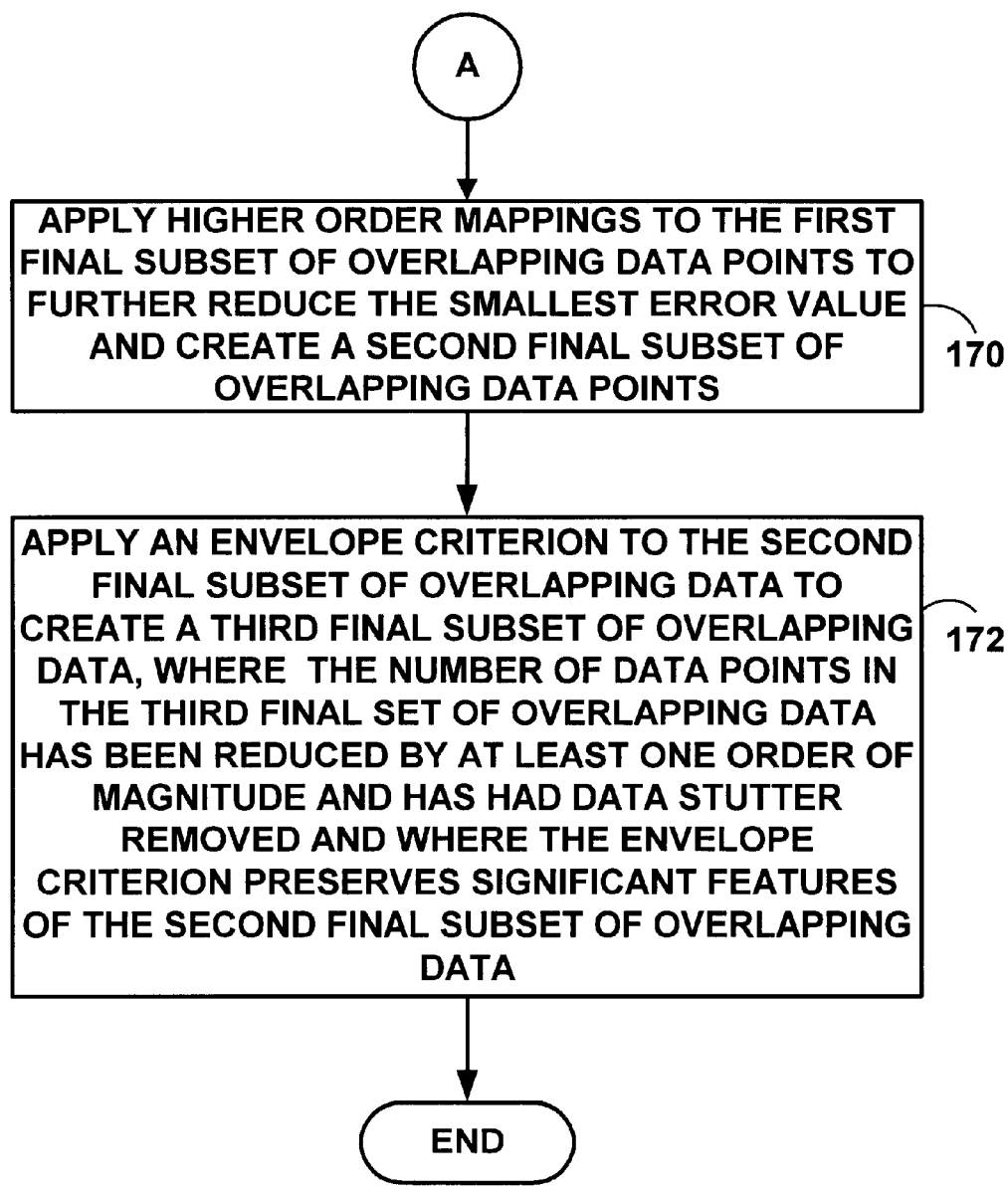

FIGS. 12A and 12B is a flow diagram illustrating a Method 162 for processing experimental data. At Step 164, of FIG. 12A, a multi-component data signal is read. The multi-component data signal includes multiple individual data signal components of varying spectral characteristics and varying amplitudes. The multiple individual data signal components overlap within portions of the multi-component data signal. At Step 166, filters are applied to the multi-component data signal to create multiple non-overlapping individual data signal components. The filter also filters multiple signal artifacts in the multi-component data signal that introduce ambiguity to base values in the multiple non-overlapping individual data signal components to spatially detrend and normalize the multiple non-overlapping individual data signal components to a uniform set of base values. At Step 168, multiple linear mappings are applied to multiple overlapping subsets of data points from the multiple non-overlapping individual data signal components to select a first final subset of overlapping data points with a smallest error value. The data points in the first final subset of overlapping data points include data points that fall within a standardized range and wherein false data points have been removed.

At Step 170 of FIG. 12B, multiple higher order mappings are applied to the first final subset of overlapping data points to further reduce the smallest error value for the final subset of overlapping data points and create a second final subset of data points. At Step 172, an envelope criterion is applied to compress the number of data values in the second final subset of overlapping data by at least an order of magnitude, reduce data stutter, and create a third final subset of overlapping data. Significant features of the second final subset of overlapping data are preserved within the envelope criterion. The third final subset of overlapping data is suitable for the windowed display 16 on the display device 14.

Method 162 allows the processing of multi-component data signals from biotechnology experiments or experiments from other arts to be automated. When a multi-component data signal is input, a third final subset of overlapping data with multiple data peaks suitable for display on a windowed device is automatically produced. This may help reduce or eliminate inconsistencies in experimental data processing that typically lead to unreliable or erroneous results.

In one exemplary preferred embodiment of the present invention, the multi-component data signal includes multi-component fluorescence intensities for polynucleotide data including DNA, cDNA or mRNA. However, the present invention is not limited to multiple-component data signals for polynucleotide data, or other biotechnology data, and multi-component data signals from other arts can also be used (e.g., telecommunications signals, electrical signals data for electrical devices, optical signals, physical signals, or other data signals).

In yet another exemplary preferred embodiment of the present invention, Method 162 is accomplished by applying Method 20 (FIG. 2) at Steps 164, 166 (FIG. 12A), Method 74 (FIG. 4) at Step 168 (FIG. 12A), Method 130 (FIG. 8) at Step 170 (FIG. 12B), and Method 146 (FIG. 10) at step 172 (FIG. 12B). However, the present invention is not limited to applying all the steps of these methods to accomplished Method 162 (FIGS. 12A and 12B). Method 162 can be accomplished by applying selected steps from these methods.

FIGS. 13A and 13B are block diagrams 174, 176 illustrating Method 162 of FIGS. 12A and 12B. FIG. 13A illustrates a multi-component data signal 178 of interest. FIG. 13B illustrates set of processed desired data peaks 180, 182, 184, 186, 188, 190, 192, 194, 196, 198, 200 from the multi-component data signal 178 after processing with Method 162. The multi-component data signal has been filtered, normalized to a predetermined size, had false peaks, errors and data stutter removed, has been smoothed, and had the number of data values reduced by at least one order of magnitude. The processed desired data peaks are suitable for display on the windowed display 16 of the display device 14.

In one exemplary preferred embodiment of the present invention, the desired data peaks 180, 182, 184, 186, 188, 190, 192, 194, 196, 198 and 200 (FIG. 13B) are polynucleotide fragment peaks (e.g., DNA, cDNA or mRNA). However, the present invention in not limited to multi-component data signals including polynucleotide fragment data and other multi-component data signals including other experimental information could also be used (e.g., telecommunications signals, electrical signals data for electrical devices, optical signals, physical signals, or other data signals).

Exemplary Multi-component Data Processing System

Figure 14:
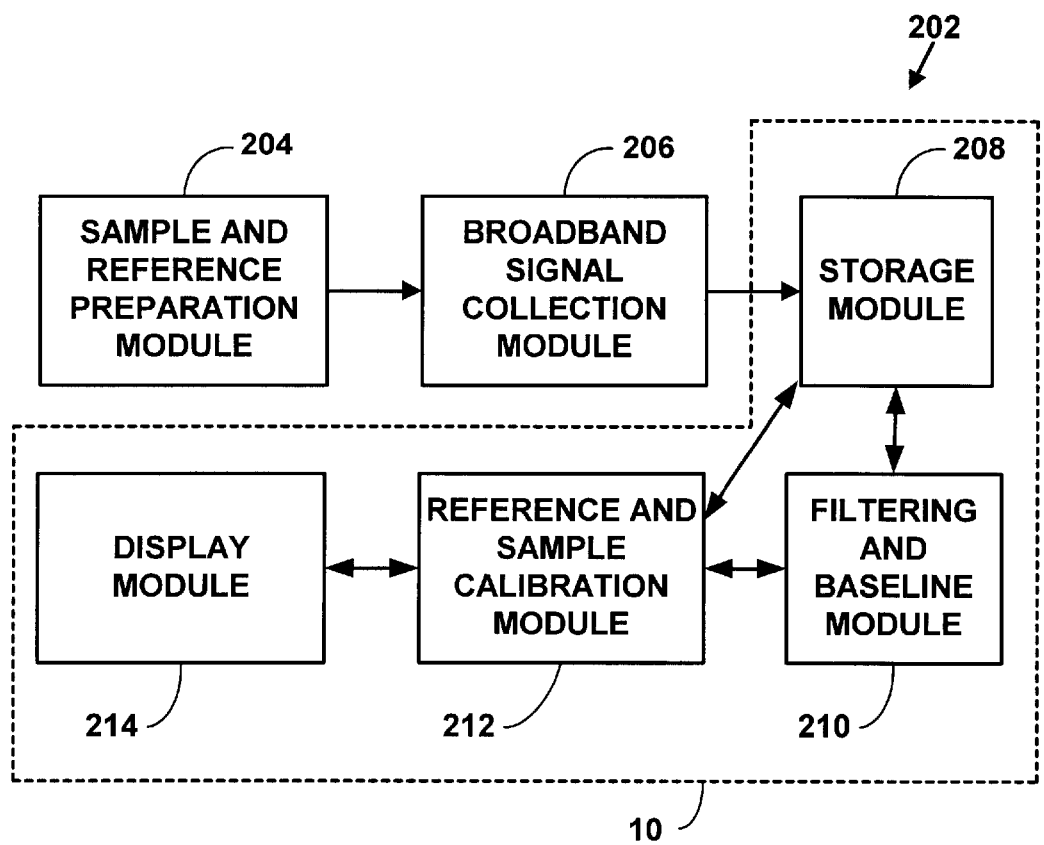
FIG. 14 is a block diagram illustrating an exemplary multi-component signal data processing system.

FIG. 14 is a block diagram illustrating an exemplary multi-component data processing system 202. The multi-component data processing system includes a data sample and reference calibration module 204, an optional broadband signal collection module 206, a storage module 208, a filtering and baseline module 210, a reference and sample calibration module 212 and a display module 214.

The data sample and reference calibration module 204 is used for processing known and target biotechnology samples. The optional broadband signal collection module 206 is used for collecting experimental data from multi-component data signals when laser-induced fluorescence of biotechnology products is used. In another embodiment of the present invention, the optional broadband signal collection module 206 can be eliminated if other technologies are used instead of laser-induced fluorescence (e.g., micro-arrays). The storage module 208 is used to store experimental data. The filtering and baseline module 210 is used to remove spectral overlap and normalize experimental data if laser-induced fluorescence is used, or can be used to perform other filtering and baselines if other technologies are used (e.g., micro-arrays).

The reference and calibration module 212 is used for standard size detection with false peak and clutter removal, data size calibration, envelope detection and data stutter removal of experimental data. The display module 214 visual displays processed experimental data. However, the present invention is not limited to these modules and more or fewer modules could also be used. In additional, the functionality of the modules described could be combined or split into additional modules.

In one exemplary preferred embodiment of the present invention, experimental data processing system 10 (FIG. 1) includes the storage module 208, the filtering and baseline module 210, the reference and sample calibration module 212 and the display module 214 (FIG. 14) as an integral combination of hardware and software (i.e., indicated by the dashed line in FIG. 14). This allows virtually any experimental technique (e.g., gel-electrophoresis, miro-arrays, etc.) to be used to generate data files that are stored in the storage module 208 and processed with the methods described herein with software resident on the computer 12. Such an embodiment provides flexibility to process experimental data from a wide variety of applications on a conventional personal computer system, or other larger computer system.

The methods and system described herein are used to process data for display on the windowed display 16 of display device 14, as is illustrated by FIG. 13B. However, a final processed set of data (e.g., the third final subset of data) may still require additional processing for visual display and comparative analysis.

Display of Processed Experimental Data

As was discussed above, "raw" experimental data starting with multi-component data signals can be processed with one or more methods to produce a "processed" set of data suitable for visual display. Some of the problems associated with processing such raw experimental data are overcome in co-pending application Ser. No. 09/318,699, filed May 25, 1999, assigned to the same Assignee as the present application.

In one exemplary preferred embodiment of the present invention, the methods illustrated in FIG. 2, FIG. 4, FIG. 8, and FIG. 10, or FIGS. 12A and 12B are used to produce multiple final sets of processed experimental data from raw experimental data. The multiple final sets of processed experimental data are typically grossly suitable for visual display, comparative analysis or other analysis. However, the present invention is not limited to using the methods illustrated in FIG. 2, FIG. 4, FIG. 8, and FIG. 10, or FIGS. 12A and 12B, and other methods could be used to produce a final set of processed experimental data from raw experimental data.

In exemplary preferred embodiments of the present invention, the multiple final sets of processed experimental data are indexed with one or more sample indices to create multiple indexed data sets that are suitable for visual display and comparative analysis. Preferred embodiments of the present invention are used to further process the multiple indexed data sets grossly suitable for visual display or comparative analysis to help overcome "experiment-to-experiment variability."

As was discussed above, one of the most commonly used methodologies in biotechnology is "comparison." Visual display of biotechnology data is typically recognized as typically being "necessary" for biotechnology research. If experimental data can be consistently collected, processed and displayed with a high degree of confidence that the results are accurate and not subject to experiment-to-experiment variability an intended result may be achieved in a quicker and more appropriate manner. For example, a sequence for a polynucleotide may be established with fewer experiments with a higher level of confidence in results.

Normalizing Processed Experimental Data

Processed experimental data typically comes from different experimental environments (e.g., different electrophoresis-gels or micro-arrays). The specific processes used to produce processed experimental data represented in any given experimental data set will typically differ from experiment-to-experiment. This variability can be of a same order of magnitude as data of interest. Thus, when processed experimental data is displayed from a same experiment completed multiple times with the same target, experiment-to-experiment variability may overwhelm data of interest.

When differential display techniques are used for analysis of experimental data, it is implicit in a differential display technique that a first set of processed experimental data displayed should have similar characteristics to a second set of experimental data (e.g., a similar scale or baseline) for a same experiment with a same target. Otherwise any significance of any variability revealed by the differential comparison would be inherently ambiguous.

In one exemplary preferred embodiment of the present invention, gross measurements of an essential centrality of significant features in indexed data sets are created. For example, a "mode" value from a centrality of significant features in an indexed data set is created. As is known in the art, a mode is a most frequent value in a set of data or a value for which a function used to define a set of data points achieves a maximum value. This mode value is called a "central character." A carefully constrained demodulation of a coarse-grained departure of any given indexed data set from this central character has been determined experimentally to remove experiment-to-experiment variability.

Part of the effectiveness of such normalization is dependent upon a utility and an accuracy with which the central character is identified as well as an extent to which fine-grained departures of each indexed set of data points are preserved. For example, if biotechnology data from polynucleotides is being used, it is desirable to compare fluorescence intensity peaks for polynucleotide fragments of a same size. It is also desirable to identify any patterns in relative heights of fluorescence peaks as indicators of relative numbers of polynucleotide fragments. Thus, measures of centrality are formed from experiment specific, inter-trace ratios of smoothed versions of size-calibrated fluorescence trace envelopes. Such measures of centrality are used to create a central character. However, the present invention is not limited to biotechnology experimental data, and other experimental data could also be used.

Figure 15:
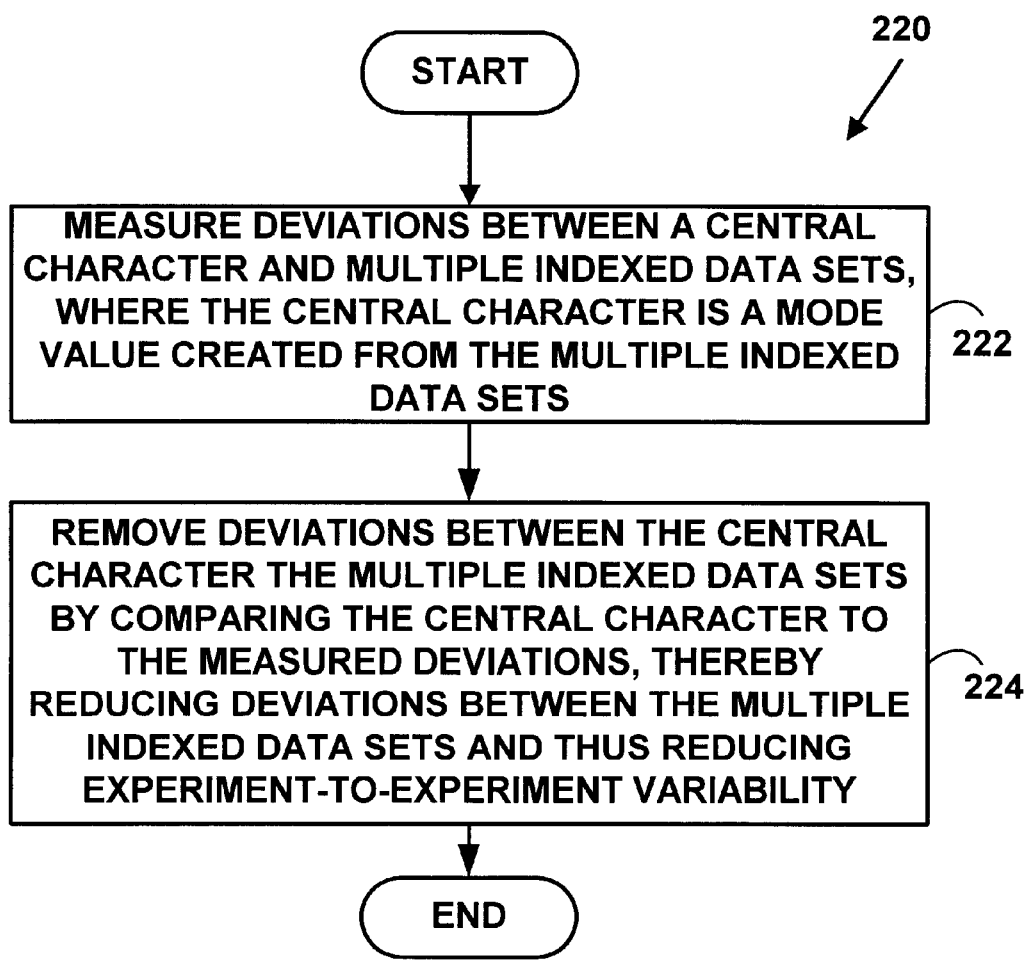
FIG. 15 is a flow diagram illustrating a method for normalization of experimental data.

FIG. 15 is a flow diagram illustrating a Method 220 for normalization of experimental data. Sets of processed experimental data are indexed with one or more indices to create multiple indexed data sets that are suitable for visual display and comparative analysis. However, other data organization schemes could also be used and the present invention is not limited to using indices for multiple sets of experimental data. At Step 222, deviations are measured from a determined central character and data values from the multiple indexed data sets. In one exemplary preferred embodiment of the present invention, the determined central character is a "mode" value of an ordered comparison determined from the multiple indexed data sets. However, other types of central characters can also be used and the present invention is not limited to central character that is a mode.

At Step 224, deviations between the central character and the multiple indexed data sets are removed by comparing the central character to the measured deviations from the multiple indexed data sets. Deviations between the multiple indexed data sets are reduced and thus, experiment-to-experiment variability is reduced between the multiple indexed data sets.

In one exemplary preferred embodiment of the present invention, the multiple indexed data sets include polynucleotide data. The polynucleotide data includes, but is not limited to, DNA, cDNA or mRNA data. However, the present invention is not limited to multiple indexed data sets that include polynucleotide data, and other indexed data sets of experimental data can also be used.

Method 220 helps reduce experiment-to-experiment variability by reducing deviations between multiple indexed data set introduced into the multiple data sets by experimental variability of individual experiments. Method 220 allows multiple indexed data sets to be visually displayed on the windowed display 16 on the display device 14 to be used for comparative analysis.

In one exemplary preferred embodiment of the present invention, at Step 222 a normalization transform is applied to the multiple indexed data sets to utilize data information across indices from the multiple indexed data sets. This normalization transform can also be used to determine a central character. The normalization transform includes any of a zero-order transform or a low-order transform.

In another exemplary preferred embodiment of the present invention, a determined zero-order central character is multiplied across data values in the multiple indexed data sets as a data-value-independent constant to normalize data points in the multiple indexed data sets. In yet another exemplary preferred embodiment of the present invention, a determined low-order central character is multiplied across data values in the indexed data sets as a data-value-dependent smoothly varying scaling function to normalize data points in the multiple indexed data sets. After normalizing data points in the multiple indexed data sets with a zero-order central character or a low-order central character, data from the multiple indexed data sets are further normalized with Method 220 as described above. The zero-order and low-order transforms are explained below. However, the present invention is not limited to zero-order or low order normalization transforms and other normalization transforms can also be used to create a central character.

Zero-order Data Display Normalization

A zero-order data display normalization includes determining a zero-order central character. The transformed data points are used to determine deviations from a zero-order central character. The deviations are considered to be of "zero-order" because such central character is a "constant" that is independent of the indices of data values from the multiple indexed data sets.

Figure 16:
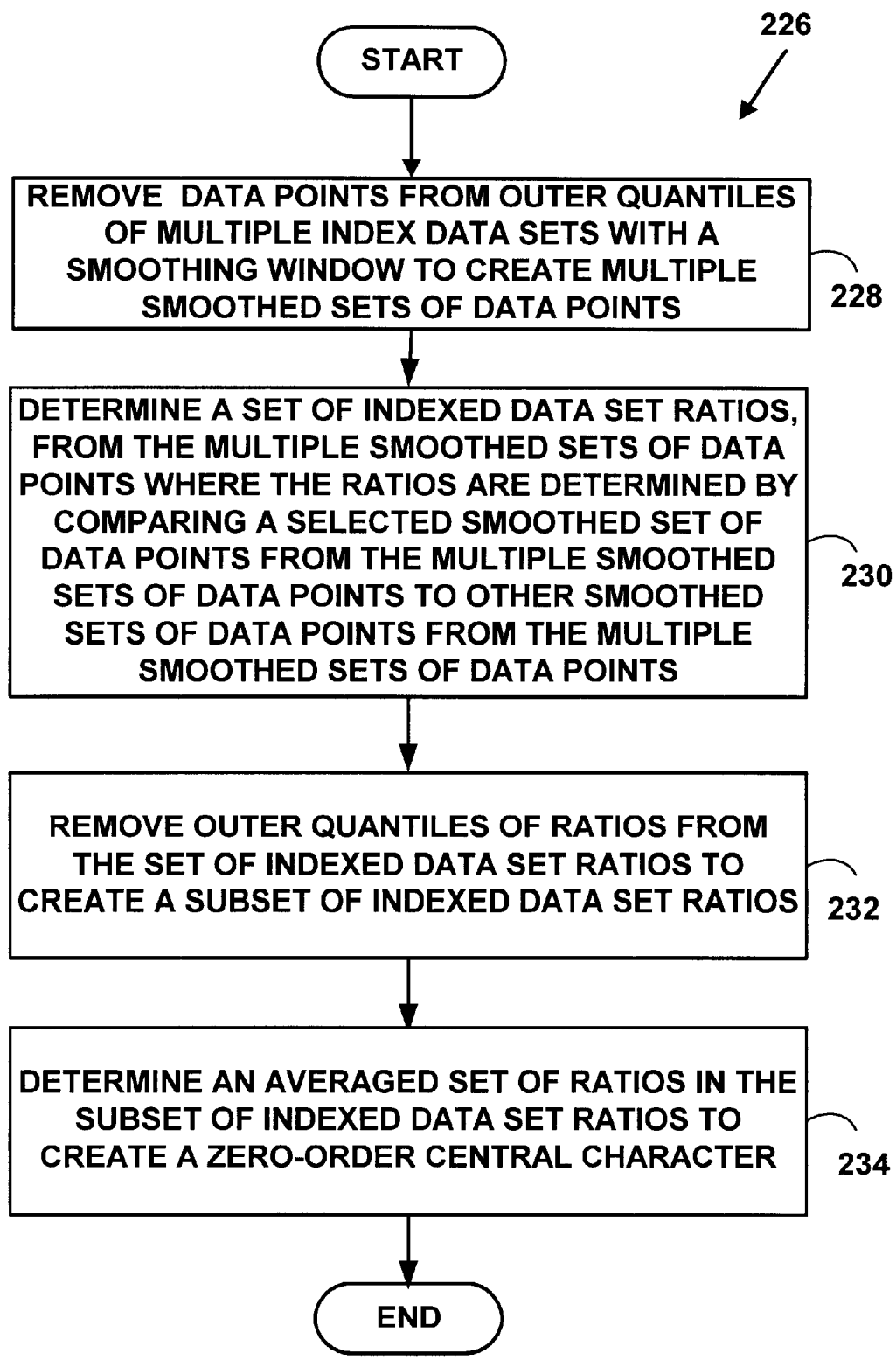
FIG. 16 is a flow diagram illustrating method for creating a zero-order central character.

FIG. 16 is a flow diagram illustrating a Method 226 for creating a zero-order central character. At Step 228, data points from outer quantiles of multiple indexed data sets are removed with a smoothing window to create multiple smoothed sets of data points for the multiple indexed data sets. At Step 230, a set of indexed data set ratios is determined from the multiple smoothed sets of data points. The set of indexed data set ratios is determined by comparing a selected smoothed set of data points from a selected indexed data set to other smoothed sets of data points from other indexed data sets from the multiple indexed data sets. At Step 232, outer quantiles of ratios are removed from the set of indexed data set ratios to create a subset of indexed data set ratios. At Step 234, an averaged set of ratios is determined from the subset of indexed data set ratios to create a zero-order central character.

Method 226 is used to create a zero-order central character to reduce experiment-to-experiment variability. In one exemplary preferred embodiment of the present invention, a created zero-order central character is multiplied across data values in the multiple indexed data sets as a data-value-independent constant to normalize data points in the multiple indexed data sets before removing deviations (e.g., with Method 220) with the zero-order central character. In another embodiment of the present invention, a created zero-order central character is not multiplied across data values in the multiple indexed sets, but is still used to reduce experiment-to-experiment variability (e.g., with Method 220).

In one exemplary preferred embodiment of the present invention, the multiple indexed data sets include polynucleotide data. The polynucleotide data includes, but is not limited to DNA, cDNA or mRNA data.

In one exemplary preferred embodiment of the present invention, at Step 228 data points from outer quantiles of the multiple indexed data sets are removed with a smoothing window. As is known in the art, a distribution can be summarized in a few numbers, for ease of reporting or comparison. One method is to use "quantiles." Quantiles are values that divide a distribution such that there is a given proportion of observations below the quantile. For example, a median is a quantile. The median is a central value or central character of a distribution, such that half the points are less than or equal to the central value and half are greater than or equal to it.

In one exemplary preferred embodiment of the present invention, a triangular window is used to smooth envelopes of sets of size-calibrated data points in a given indexed set of data points. However, other methods can also be used to smooth a trace envelope and the present invention is not limited to a triangular smoothing window and other smoothing windows could also be used.

In one exemplary preferred embodiment of the present invention, outer quantile values are removed from multiple indexed data sets with a smoothing window as is illustrated in Equation 13. A smoothing window has a width P. In one specific exemplary preferred embodiment of the present invention, P is an odd positive integer greater than or equal to three. However, the present invention is not limited to a smoothing window with a window size of odd positive integer greater than or equal to three and other smoothing window sizes could also be used (e.g., even positive integers).

A smoothed version of a trace envelope $f^{**}_k$ is found with a smoothing window as illustrated in Equation 13. However, other smoothing windows could also be used.

$$f^{**}_k = [2/(P+2)]\Sigma_{p=-[P/2],\ldots,[P/2]}[((P+2)-|p|)/(P+2)]f^*_{k+p} \quad (13)$$

At Step 230, a set of indexed data set ratios is determined. At Step 232, outer quantiles of ratios are removed from the set of indexed data set ratios to create a subset of indexed data set ratios. With $g^{}_k$ generically designating a smoothed envelope for another set of indexed data points and $D_s(f^{})$ an s-th quantile of the values of a smoothed trace envelope $f^{**}$, ratios $r_k(g,f)$ for multiple indexed data sets are formed as illustrated in Equation 14. However, the present invention is not limited to the ratios illustrated in Equation 14 and other ratios could also be formulated and used.

$$r_k(g,f)=\{g^{}_k/f^{}_k:D_s(f^{})\leq f^{}_k\leq D_t(f^{});D_s(g^{})\leq g^{}_k\leq D_t(g^{})\} \quad (14)$$

At Step 234, an averaged set of ratios is determined from ratios from the subset of indexed data set ratios determined with Equation 14. Using $D_u(r(g,f))$ as a u-th quantile of the ratios of smoothed trace envelopes f and g, a zero-order normalization of a scale factor, $\lambda_0(f)$, for a central character for a trace envelope $f^{**}_k$ is an average over inner quantiles of the ratios and over other distinct indexed data sets as is illustrated by Equation 15. However, other zero-order normalization scale factors for a central character could also be used, the present invention is not limited to the zero-order normalization scale factor illustrated in Equation 15. Equation 15 removes outer quantile values of ratios of the multiple indexed data sets ratios and averages the remaining indexed data set ratios not in a removed outer quantile to create an average set of ratios at Step 234.

$$\lambda_0(f)=\mathrm{avg}(\forall k,\ g\neq f)\{r_k(g,f):D_u(r(g,f))\leq r_k(g,f)\leq D_v(r(g,f))\} \quad (15)$$

Although s and u or t and v are not directly related, in one specific exemplary preferred embodiment of the present invention, it has been determined experimentally that percentiles for the outer quantiles are reasonably well-defined using s=u=6 and t=v=95, wherein 6 and 95 represent a $6^{th}$ percentile and a $95^{th}$ percentile respectively in an indexed set of data points. Thus, the smallest 6% and the largest 5% of the ratios are removed. However, other percentile values could also be used for s and u and t and v, and the present invention is not limited to these specific values for s and u and t and v.

Figure 17:
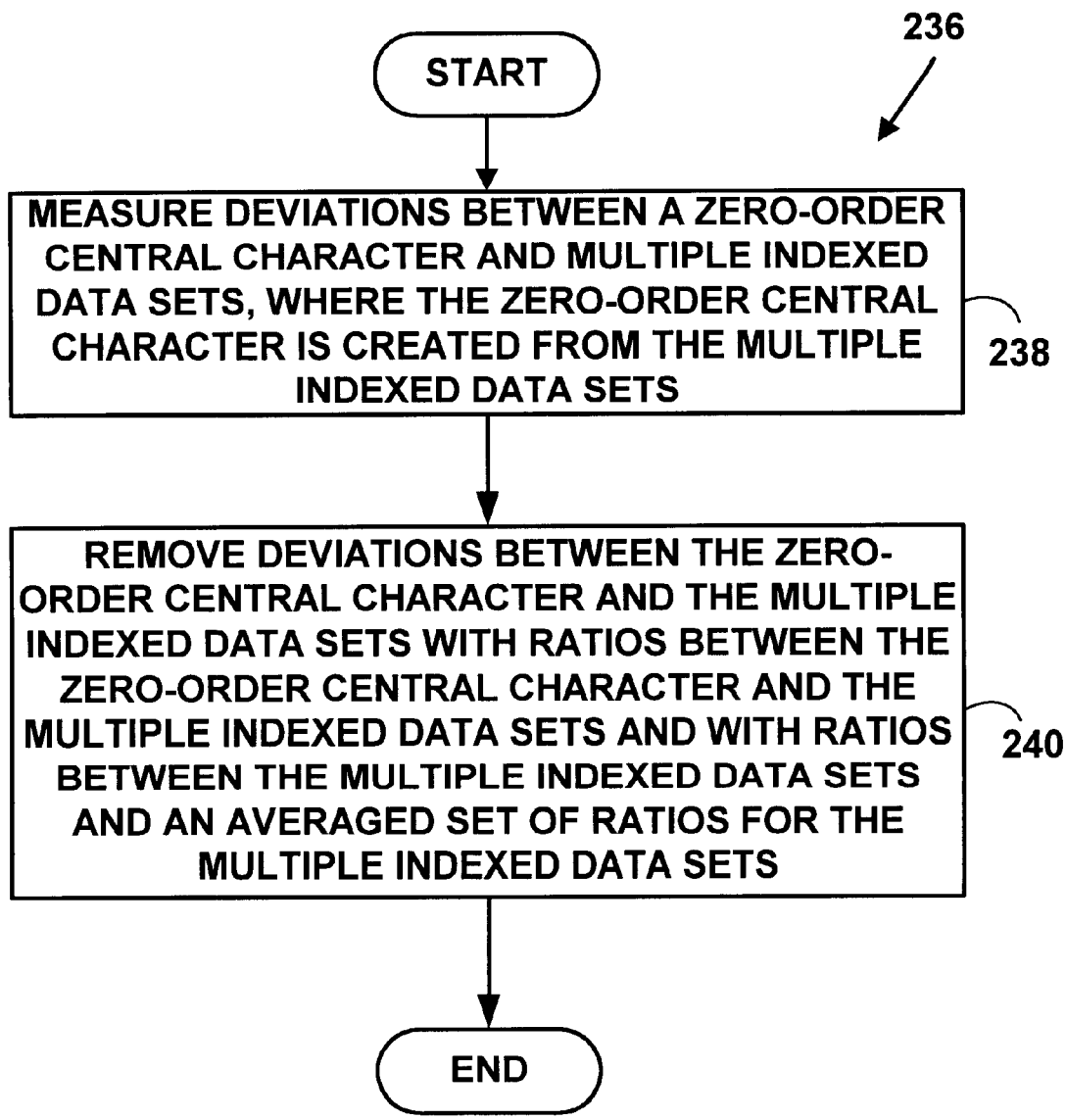
FIG. 17 is a flow diagram illustrating method for normalization of display data using a zero-order central character.

FIG. 17 is a flow diagram illustrating a Method 236 for normalization of display data using a zero-order central character. At Step 238, deviations are measured from a zero-order central character and multiple indexed data sets. The zero-order central character is determined from the multiple indexed data sets (e.g., with Method 226 of FIG. 16). At Step 240, deviations are removed between the zero-order central character and the multiple indexed data sets with ratios between the zero-order central character and the multiple index data sets and with ratios between the multiple indexed data sets and an averaged set of ratios for the multiple indexed data sets ratios.

In one exemplary preferred embodiment of the present invention, the multiple indexed data sets include polynucleotide data. The polynucleotide data includes, but is not limited to, DNA, cDNA or mRNA data.

In one exemplary preferred embodiment of the present invention, at Step 238 of Method 236 (FIG. 17) deviations from a zero-order central character are determined using a zero-order central character, for example, with $\lambda_0(f)$, from Equation 15. However, other zero-order central characters could also be used in Method 236. At Step 240, deviations are removed between the central characters and the multiple indexed data sets by finding ratios of the multiple index data sets to the zero-order central character as is illustrated by Equation 14. Deviations are removed using the multiple indexed data sets and an averaged set of ratios as is illustrated with Equation 15.

Method 236 (FIG. 17) with a zero-order central character helps reduce experiment-to-experiment variability by reducing deviations between multiple indexed data sets introduced into the indexed data sets by individual experiments using a central character created by a data-value-independent zero-order normalization of multiple indexed sets of data.

Low-order Data Display Normalization

A low-order display normalization is a generalization of the zero-order Method 226 illustrated in FIG. 16. In one exemplary preferred embodiment of the present invention, a low-order central character is used instead of a zero-order central character. The low-order normalization produces a smoothly varying scaling function with a very low-order dependence upon indexed data set data values (e.g., polynucleotide fragment sizes). The data-value-dependent low-order central character (FIG. 18) can be contrasted with a data-value-independent constant scaling factor produced by the zero-order Method 226 (FIG. 16).

Figure 18:
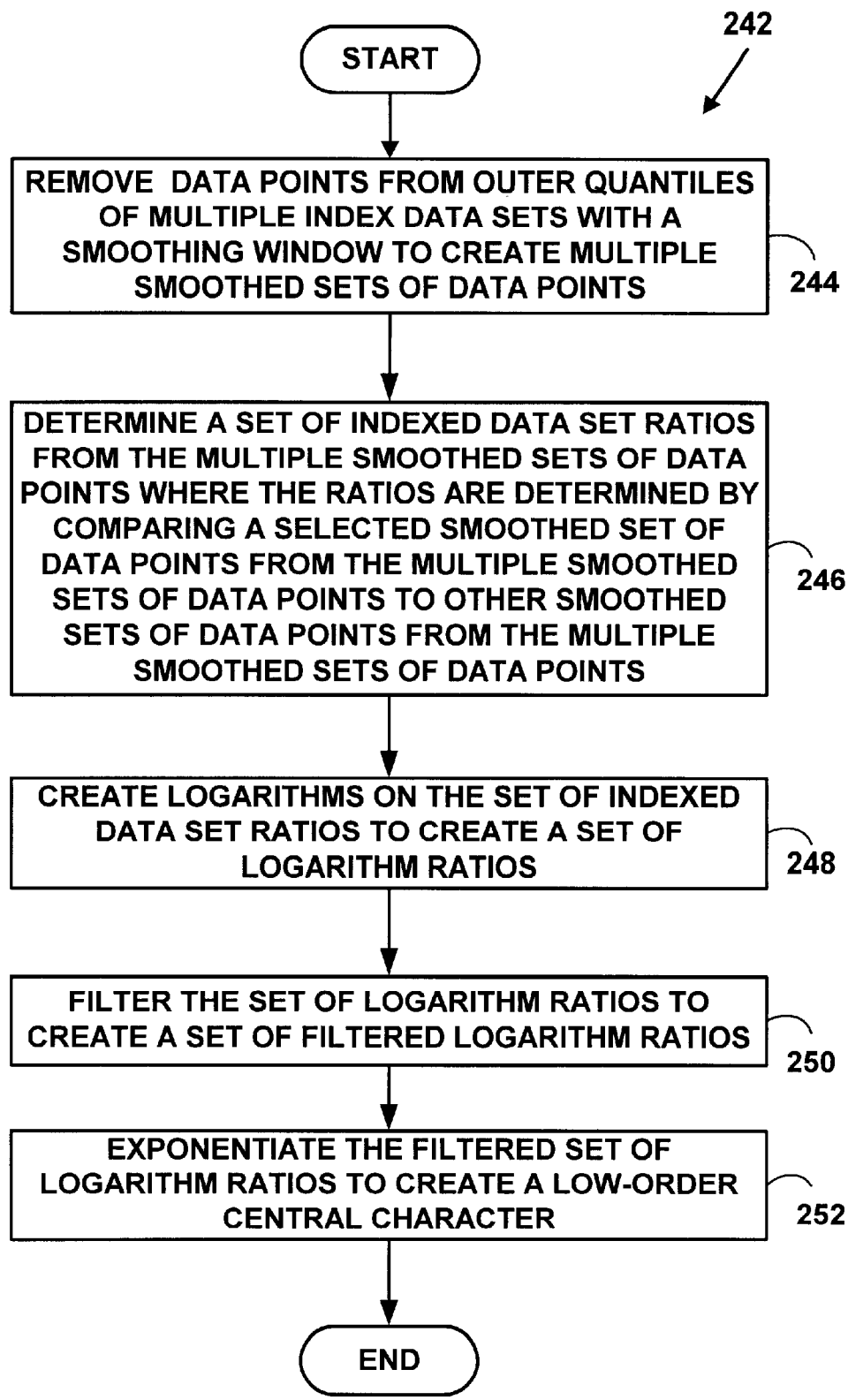
FIG. 18 is a flow diagram illustrating a method for creating a low-order central character.

FIG. 18 is a flow diagram illustrating a Method 242 for determining a low-order central character. At Step 244, data points from outer quantiles of the multiple indexed data sets are removed with a smoothing window to form multiple smoothed sets of data points for the multiple indexed data sets. At Step 246, a set of indexed data set ratios is determined from the multiple smoothed sets of data points by comparing a selected smoothed set of data points from a selected index data set to other smoothed sets of data points from other indexed data sets from the multiple indexed data sets. At Step 248, logarithms are created on the set of indexed data set ratios to create a set of logarithm ratios. At Step 250, the set of logarithm ratios is filtered to create a filtered set of logarithm ratios. At Step 252, an exponentiation is applied to an average of the filtered set of logarithm ratios to create a low-order central character.

In one exemplary preferred embodiment of the present invention, the multiple indexed data sets include polynucleotide data. The polynucleotide data includes, but is not limited to, DNA, cDNA or mRNA.

In one exemplary preferred embodiment of the present invention, a created low-order central character is multiplied across data values in the multiple indexed data sets as a data value dependent smoothly varying scaling function. The low-order central character may be used to transform data points in the multiple indexed data sets before removing deviations (e.g., with Method 220) with the low-order central character. In another embodiment of the present invention, a created low-order central character is not multiplied across data values in the multiple indexed sets, but is still used to reduce experiment-to-experiment variability.

For any given indexed data set, a low-order size-dependent scaling function is created by using a smoothing window (e.g., from Equation 13) to smooth envelopes of size-calibrated data values at Step 242. In one preferred embodiment of the present invention, Step 244 (FIG. 18) is the same as Step of 228 of Method 226 (FIG. 16) (See, e.g., Equation 13). However, other smoothing windows could also be used. At Step 246, a set of indexed data set ratios is determined by comparing a selected smoothed set of data points from a selected index data set to other smoothed sets of data points from other indexed data sets from the multiple indexed data sets. In one preferred embodiment of the present invention, this is the same as Step 230 of Method 226 (See, e.g., Equation 14). However, other ratios could also be used.

At Step 248, logarithms for a desired base-x are formed on the set of indexed data set ratios to create a set of logarithm ratios. As is known in the art, a logarithm (denoted generally as "log(x)") is an exponent or a power to which a given base-x must be raised to produce another number. In one exemplary preferred embodiment of the present invention, a log to the base e is used where e is the well known mathematical irrational number 2.718281828459045 . . . At Step 250, the set of logarithm ratios is filtered to create a filtered set of logarithm ratios. In one exemplary preferred embodiment of the present invention, the filtering includes applying a "low pass filter." However, other filters can also be used and the present invention is not limited to low pass filters. As is know in the art, a low pass filter-$\omega_L$ "passes" data whose frequencies $\omega$ fall within a range $0 \leq \omega \leq \omega^c$, and rejects data whose frequencies are greater than $\omega_c$, wherein $\omega_c$ is a cutoff frequency.

In one exemplary preferred embodiment of the present invention, a low pass filter is achieved by using a tapered notch in a frequency domain, which provides an explicit means for manipulating variability demodulated by a low-order normalization. For example, the tapered notch provides constraints via a size-scale equivalence of a relative placement of a center of a frequency-domain filter edge. A filter edge is chosen to ensure that the dampened variability is of a size-scale no finer than a significant fraction of a full size range on the display device 14. Such scaling functions have very smooth and well-behaved dependence upon data size (e.g., polynucleotide fragment size). Note that the zero-order Method 226 occurs as a special case of the low-order method which is obtained by setting an edge of the low pass filter to exclude all variation that has any dependence upon data size.

At Step 250, with $f^{}_k$ a smoothed envelope for one specific indexed data set and $g^{}_k$, for another indexed data set other than $f^{**}_k$, a filtered set of logarithmic ratios is created as is illustrated in Equation 16. In one exemplary preferred embodiment of the present invention, the filter is a low pass filter as described above. However, other filters could also be used (e.g., high-pass, band-pass, etc). In addition, the present invention is not limited to the filtered set of logarithmic ratios illustrated in Equation 16 and other filtered ratios could also be used.

$$\rho_k = \chi_\omega[log x(g^{}_k / f^{}_k)] \tag{16}$$

In one exemplary preferred embodiment of the present invention, a filter $\chi_\omega$ is applied in a frequency domain using a discrete Fourier transform to create a filtered set of logarithmic ratios $\rho_k$. The filter $\chi_\omega$, is a tapered low-pass filter whose notch mask is multiplied into a zero-padded discrete Fourier transform of the logarithmic ratios. Significant features of a tapered mask are a degree of tapering and placement of an exclusion edge. In one exemplary preferred embodiment of the present invention, a conventional two-percent "Tukey taper" is applied to an edge whose half-height (a so-called '3 dB point') is set on a ninth-bin of a discrete transform, which is zero-padded by a factor of four. A Tukey taper is known to those skilled in the filtering arts. However, other tapers and filters could also be used for filter $\chi_\omega$ and the present invention is not limited to low pass filters or to Tukey tapers of low pass filters.

At Step 252, an exponentiation for a desired base-x is applied to an average of a filtered set of logarithm ratios to create a low-order central character, $\lambda_k(f)$. As is known in the art, an exponentiation is an "inverse" of a logarithm.

The low-order central character, $\lambda_k(f)$, is a size-dependent, low-order normalization scaling function for a smoothed envelope $f^*_k$. The low-order central character, $\lambda_k(f)$, is an exponentiated average of the set of filtered logarithmic ratios over all other $k^{th}$ indexed data sets, as is illustrated in the low-order central character of Equation 17. However, the present invention is not limited to Equation 17, and exponentiations can also be used.

$$\lambda_k(f) = \exp_x[\text{avg}(\forall k, g \neq f)\{\rho_k(g, f)\}/2] \tag{17}$$

In one exemplary preferred embodiment of the present invention, the filter $\chi_\omega$ restricts a size-scale of variability demodulated by a low-order central character, $\lambda_k(f)$, to no smaller than about half a full range of a display size-axis on the display device 16. A zero-padding with a tapered filter edge enhances the smoothness of a resulting low-order central character by including increasingly smaller elements of smaller scale variability.

Figure 19:
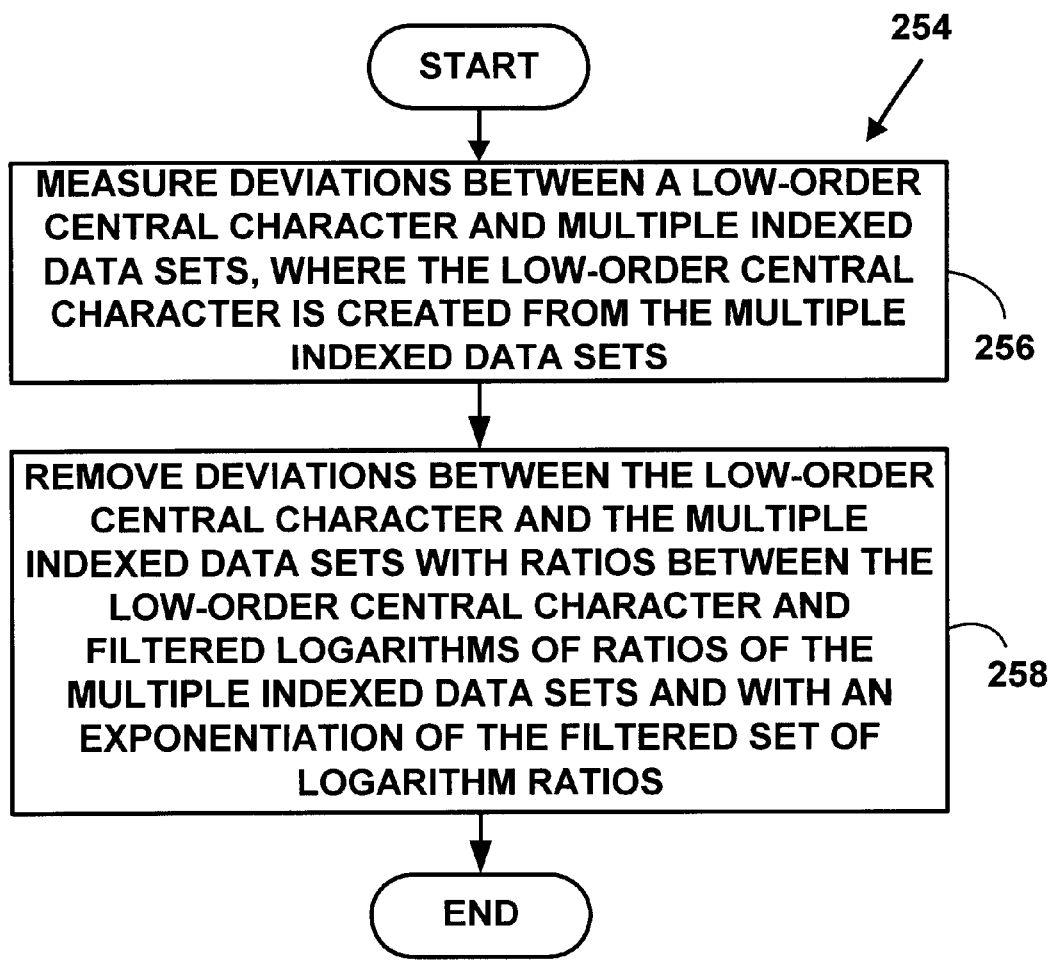
FIG. 19 is a flow diagram illustrating method for normalization of display data using low-order central character.

FIG. 19 is a flow diagram illustrating a Method 254 for normalization of display data using a low-order central character. At Step 256, deviations are measured from a low-order central character and multiple indexed data sets. The low order character is determined from the multiple indexed data sets (e.g., with Method 242 of FIG. 18). At Step 258, deviations are removed between the low-order central character and the multiple indexed data sets with ratios between the low-order central character and filtered logarithms of ratios for the multiple indexed data sets and with exponentiations of a filtered set of logarithms of ratios.

In one exemplary preferred embodiment of the present invention, the multiple indexed data sets include polynucleotide data. The polynucleotide data includes, but is not limited to, DNA, cDNA or mRNA.

Method 254 (FIG. 19) with a low-order central character helps reduce experiment-to-experiment variability by reducing deviations between multiple indexed data set introduced into the indexed data sets by individual experiments using a central character created by a data-value-dependent low-order normalization of multiple indexed sets of data.

Exemplary Normalized Experimental Data Display Output

FIG. 20A is a block diagram illustrating a portion of an exemplary output display 262 for an indexed set of control data for an illustrative experiment (e.g., data peaks 180, 182, and 184 of FIG. 13B). The output display 262 is not normalized. FIG. 20B is a block diagram illustrating a portion of an exemplary output display 264 for an indexed data set for a first target for the illustrative experiment (e.g., a first target polynucleotide sequence). The output display 264 is not normalized. In a preferred embodiment of the present invention, either a zero-order central character or a low-order central character is used to normalize experimental results.

FIG. 20C is a block diagram illustrating a portion of an exemplary output display 266 for an indexed data set of control data from FIG. 20A normalized with a zero-order normalization (e.g., Method 236, FIG. 17). FIG. 20D is a block diagram illustrating a portion of an exemplary output display 268 for an indexed set of target data from FIG. 20A normalized with a low-order normalization (e.g., Method 254, FIG. 19).

FIG. 20E is a block diagram illustrating a portion of an exemplary output display 270 for an indexed data set for the first target from FIG. 20B normalized with a low-order normalization (e.g., Method 250 FIG. 19). FIG. 20F is a block diagram illustrating a portion of an exemplary output display 272 for an indexed data set for the first target from FIG. 20B normalized with a low-order normalization (e.g., Method 250 FIG. 19). A width for data peaks in FIGS. 20A–20F is expanded for the purposes of illustration. However, actual display output in the windowed display 16 on the display device 14 for data peaks is similar to those in FIG. 13B.

The four normalized output displays 266, 268, 270 and 272 correspond to a normalized control 258 and a normalization of one experimental variation 260 for a first target. The output in each of the normalized displays 266, 268, 270 and 272 distinguished by solid and dashed lines respectively, represent independent replications of a sample, in general differing at least in a physical gel from which they were taken (e.g., a first run and a second run). In an exemplary preferred embodiment of the present invention, output in an actual normalized display on the display device 14 typically uses different colors to illustrate display of multiple experimental results.

As is illustrated in FIG. 20A, there is an experiment-to-experiment variability in the indexed data set of control data since the two curves are separated. If there were no experiment-to-experiment variability, the two curves represented by a solid and dashed line in FIG. 20A would be superimposed. As is illustrated in FIG. 20C, a zero-order normalization reduces the experiment-to-experiment variability of the control data. The two curves in FIG. 20C that are normalized are separated by a smaller distance between the two curves from FIG. 20A that are not normalized. As is illustrated in FIG. 20D, a low-order normalization further reduces the experiment-to-experiment variability as can be seen by a smaller distance between the two curves compared to the curves in FIG. 20A.

FIG. 20E and FIG. 20F illustrate a zero-order normalization and a low-order normalization respectively for a first target. As illustrated in FIG. 20B, the first target includes more of a first type of data (e.g., a first type of polynucleotide sequence) as is illustrated by a first data peak closest to the vertical axis, and includes less of a second and third type of data represented by the next two data peaks (e.g., a second and third type of polynucleotide sequences). This can be seen observed by comparing the control data in FIG. 20A to the data displayed for the first target in FIG. 20B. As is illustrated in FIG. 20E and FIG. 20F, normalization also reduces the experiment-to-experiment variability for the first target as can be determined by a narrow separation between the two data curves represented by the solid and dashed lines in FIGS. 20E and 20F.

Since a low-order normalization typically provides slightly better results than a zero-order normalization, selecting a zero-order normalization or a low-order normalization is dependent on a number of factors including desired accuracy of display results, type of analysis required, computational time, computational environment, type of display device, size of processed indexed data set and other factors. However, selecting either a zero-order normalization or a low-order normalization helps to significantly reduce experiment-to-experiment variability compared with non-normalized data.

Preferred embodiments of the present invention allow a difference in experimental data to be determined and reduced for multiple iterations of a selected experiment as well as across multiple different iterations of experiments. For example, normalized control data in FIG. 20C or FIG. 20D for a first experiment could be compared to normalized control data for a second experiment (not illustrated in FIG. 20). The second experiment may include the same target or a different target than the first experiment, but includes the same control. Preferred embodiments of the present invention can be used to determine experiment-to-experiment variability between the first and second experiment.

In addition, normalized data for a first target in FIG. 20E or FIG. 20F in a first experiment can be compared to a first target in a different second experiment to compare results for the first target in the first experiment and in second experiment with reduced experiment-to-experiment variability. For example, results of the first experiment including FIGS. 20A, 20B, 20D and 20F are displayed in a first window of the windowed display 16 on display device 14, and results of the second experiment in a second window of the windowed display 16.

FIGS. 20A–20F illustrates exemplary output for preferred embodiments of the present invention. However, an actual output display for preferred embodiments of the present invention typically would include only normalized data and use of the present invention would be "invisible" to a user. That is, only a final output display with experiment-to-experiment variability reduced is presented to a user for comparative analysis. A user would not be presented with the un-normalized data on the display device 14 that is illustrated in FIGS. 20A and 20B. Also, only one normalization, central character, zero-order or low-order is used at any one time. However, in another preferred embodiment of the present invention, a zero-order central character and a low-order central character may be used together to normalize different selected sets of indexed data at the same time.

Preferred embodiments of the present invention allow "intra-experimental" (i.e., same experiment) and "inter-experimental" (i.e., different experiments) variability to be reduced for comparative analysis. Preferred embodiments of the present invention may also be used as an additional method to aid in an automated processing of raw experimental data (e.g., in combination with the methods illustrated in FIG. 2, FIG. 4, FIG. 8, and FIG. 10, or FIGS. 12A and 12B above).

Preferred embodiments of the present invention allow data value features that are present in processed experimental data sets, that are of a same order of magnitude as data values introduced by experiment-to-experiment variability to be normalized and used for comparative analysis. Thus, comparison of experimental results can be used with a higher degree of confidence, and an intended result may be achieved in a quicker and more appropriate manner.

For example, in the case of biotechnology, a new polynucleotide sequence may be determined with fewer experiments with a higher level of confidence in the obtained results. This new polynucleotide sequence may be used to develop new treatment for diseases, improve existing drugs, develop new drugs and as be used for other medical applications including developing a more thorough understanding of a biological organism including the polynucleotide sequence.

Exemplary preferred embodiments of the present invention have been discussed with respect to biotechnology experimental data. However, the present invention is not limited to biotechnology experimental data. Preferred embodiments of the present invention may be used to reduce experiment-to-experiment variably for telecommunications data, electrical data, optical data, physical data, or other experimental data with experiment-to-experiment variability introduced by an environment used to conduct experiments.

It should be understood that the programs, processes, methods and system described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, in other embodiments hardware implementations may alternatively be used and visa-versa.

The claims should not be read as limited to the described order or elements unless stated to that effect. Therefore, all embodiments that come within the scope and spirit of the following claims and equivalents thereto are claimed as the invention.

We claim:

1. A method for creating a low-order central character, comprising the following steps:

removing data points from outer quantiles of a plurality of indexed data sets with a smoothing window to create a plurality of smoothed sets of data points for the plurality of indexed data sets;

determining a set of indexed data set ratios from the plurality of smoothed sets of data points, wherein the set of indexed data set ratios is determined by comparing a selected smoothed set of data points from a selected indexed data set to other smoothed sets of data points from other indexed data sets from the plurality of indexed data sets;

creating logarithms of the set of indexed data set ratios to create a set of logarithm ratios;

filtering the set of logarithm ratios to create a filtered set of logarithm ratios; and applying an exponentiation to an average of the filtered set of logarithm ratios to create a low-order central character.

2. A computer readable medium having stored therein instructions for causing a central processing unit to execute the method of claim 1.

3. The method of claim 1 wherein the step of removing data points includes removing data points with:

$$f^{**}_k = [2/(P+2)]\Sigma_{p=-[P/2],\ldots,[P/2]}[(P+2-|p|)/(P+2)]f^*_{k+p},$$

wherein $f^{**}_k$ is a smoothed set of data points, P is size of a smoothing window for a set of data points-p from a $k^{th}$-indexed data set, and $f^*$ is a data envelope enclosing a set of data points-p that does not include data points from outer quantiles of the $k^{th}$-indexed data set.

4. The method of claim 1 wherein the step of determining a set of indexed data set ratios includes determining:

$$(g^{}_k/f^{}_k),$$

wherein $f^{}_k$ is a selected smoothed set of data points from a selected $k^{th}$-indexed data set, and $g^{}_k$ is another smoothed set of data points other than $f^{**}_k$.

5. The method of claim 1 wherein the step of creating logarithms of the set of indexed data set ratios to create a set of logarithm ratios includes applying:

$$\log_x(g^{k}/f^{}_k),$$

wherein $\log_x$ is a logarithm for a desired base-x, $f^{}_k$ is a selected smoothed set of data points from a selected $k^{th}$-indexed set of data points, $g^{}_k$ is another smoothed set of data points other than $f^{**}_k$.

6. The method of claim 1 wherein the step of filtering the set of logarithm ratios to create a filtered set of logarithm ratios includes applying:

$$\rho_{k(g,f)} = \chi_\omega[\log_x(g^{}_k/f^{}_k)],$$

wherein $\rho_{k(g,f)}$ is a filtered set of logarithm ratios, $\chi_\omega$ is a filter, $\log_x$ is a logarithm for a desired base-x, $f^{}_k$ is a selected smooth set of data points from a selected $k^{th}$ indexed set of data points, $g^{}k$ is another smoothed set of data points other than $f^{**}_k$.

7. The method of claim 6 wherein the filter $\chi_\omega$ is a low pass filter.

8. The method of claim 1 wherein the step of applying an exponentiation to an average of the filtered set of logarithm ratios includes applying:

$$\lambda_k(f) = \exp_x[\text{avg}(\forall k,\ g \neq f)\{\rho_k(g,f)\}/2],$$

wherein $\lambda_k(f)$ is a low-order central character, $\exp_x$ is an exponential for a desired base-x, avg is an average, and $\{\rho_k(g,f)\}$ is a filtered set of logarithm ratios for a $k^{th}$ indexed data set.

9. The method of claim 1 wherein the plurality of indexed data sets include processed polynucleotide data.

10. The method of claim 1 wherein the plurality of indexed data sets include processed polynucleotide data suitable for visual display.

11. The method of claim 9 wherein the polynucleotide data includes DNA, cDNA, or mRNA data.

* * * * *